United States Patent
Strittmatter et al.

(10) Patent No.: US 7,335,636 B2
(45) Date of Patent: Feb. 26, 2008

(54) SPRR1A AND AXONAL REGENERATION

(75) Inventors: Stephen M. Strittmatter, Guilford, CT (US); Iris E. Bonilla, New Haven, CT (US)

(73) Assignee: Yale University, New Haven, CT (US)

(*) Notice: Subject to any disclaimer, the term of this patent is extended or adjusted under 35 U.S.C. 154(b) by 125 days.

(21) Appl. No.: 10/681,398

(22) Filed: Oct. 8, 2003

(65) Prior Publication Data

US 2005/0054094 A1   Mar. 10, 2005

Related U.S. Application Data

(63) Continuation of application No. PCT/US02/12564, filed on Apr. 22, 2002.

(60) Provisional application No. 60/285,373, filed on Apr. 21, 2001.

(51) Int. Cl.
| | | |
|---|---|---|
| *A61K 39/00* | (2006.01) | |
| *A61K 39/38* | (2006.01) | |
| *A01N 37/18* | (2006.01) | |
| *C07K 14/00* | (2006.01) | |
| *C07K 16/00* | (2006.01) | |
| *C07K 17/00* | (2006.01) | |
| *C07K 5/00* | (2006.01) | |
| *C12P 21/06* | (2006.01) | |

(52) U.S. Cl. ............. 514/12; 514/13; 514/2; 424/185.1; 424/184.1; 424/198.1; 530/300; 530/324; 530/325; 435/69.1

(58) Field of Classification Search ............. None
See application file for complete search history.

(56) References Cited

FOREIGN PATENT DOCUMENTS

| WO | WO 95/13291 A1 | 5/1995 |
|---|---|---|
| WO | WO 02/085116 | 10/2002 |

OTHER PUBLICATIONS

Kartasova et al., 1996, J. Invest. Dermatology, 106, pp. 294-304.*
Hoffer et al., 1997, J. Neural Transm, 49, pp. 1-10.*
Bonilla, I.E., et al., "SPRR1A is Expressed by Axotomized Neurons and Promotes Axonal Outgrowth," *Soc. Neurosci. Abstr.* 27:670, abstract No. 258.5, Society for Neuroscience (Nov. 2001).
Bonilla, I.E., et al., "Small Proline-Rich Repeat Protein 1A Is Expressed by Axotomized Neurons and Promotes Axonal Outgrowth," *J. Neurosci.* 22(4):1303-1315, Society for Neuroscience (Feb. 2002).
Database EMBL, "*M. musculus* mRNA for SPRR1a protein," *Accession # X91824.1*, 1 page, European Molecular Biology Laboratory (Feb. 1996).
Gibbs, S., et al., "Molecular Characterization and Evolution of the SPRR Family of Keratinocyte Differentiation Markers Encoding Small Proline-Rich Proteins," *Genomics* 16:630-637, Academic Press, Inc. (Jun. 1993).
Kubo, T., et al., "Analysis of genes induced in peripheral nerve after axotomy using cDNA microarrays," *J. Neurochem.* 82:1129-1136, International Society for Neurochemistry (Sep. 2002).
Reddy, S.P.M., et al., "Structure and organization of the genes encoding mouse small proline-rich proteins, m*SPRR1A* and *1B,*" *Gene* 224:59-66, Elsevier Science B.V. (Dec. 1998).
Tanabe, K., et al., "The Small GTP-Binding Protein TC10 Promotes Nerve Elongation in Neuronal Cells, and Its Expression Is Induced during Nerve Regeneration in Rats," *J. Neurosci.* 20(11):4138-4144, Society for Neuroscience (Jun. 2000).
Tanabe, K., et al., "Expressed-sequence-tag approach to identify differentially expressed genes following peripheral nerve axotomy," *Mol. Brain Res.* 64:34-40, Elsevier Science B.V. (Jan. 1999).
De León, M., et al., "Fatty Acid Binding Protein Is Induced in Neurons of the Dorsal Root Ganglia After Peripheral Nerver Injury," *J. Neurosci. Res.* 44:283-292 (1996).
Leon, A., et al., "Dorsal Root Ganglia and Nerve Growth Factor: A Model for understanding the Mechanism of $GM_1$ Effects on Neuronal Repair," *J. Neurosci. Res.* 12:277-287 (1984).

* cited by examiner

*Primary Examiner*—Olga N. Chernyshev
(74) *Attorney, Agent, or Firm*—Cooley Godward Kronish, LLP

(57) ABSTRACT

The present invention provides polynucleotides, polypeptides, pharmaceutical compositions, and methods for modulation of nerve growth and regeneration.

7 Claims, 21 Drawing Sheets

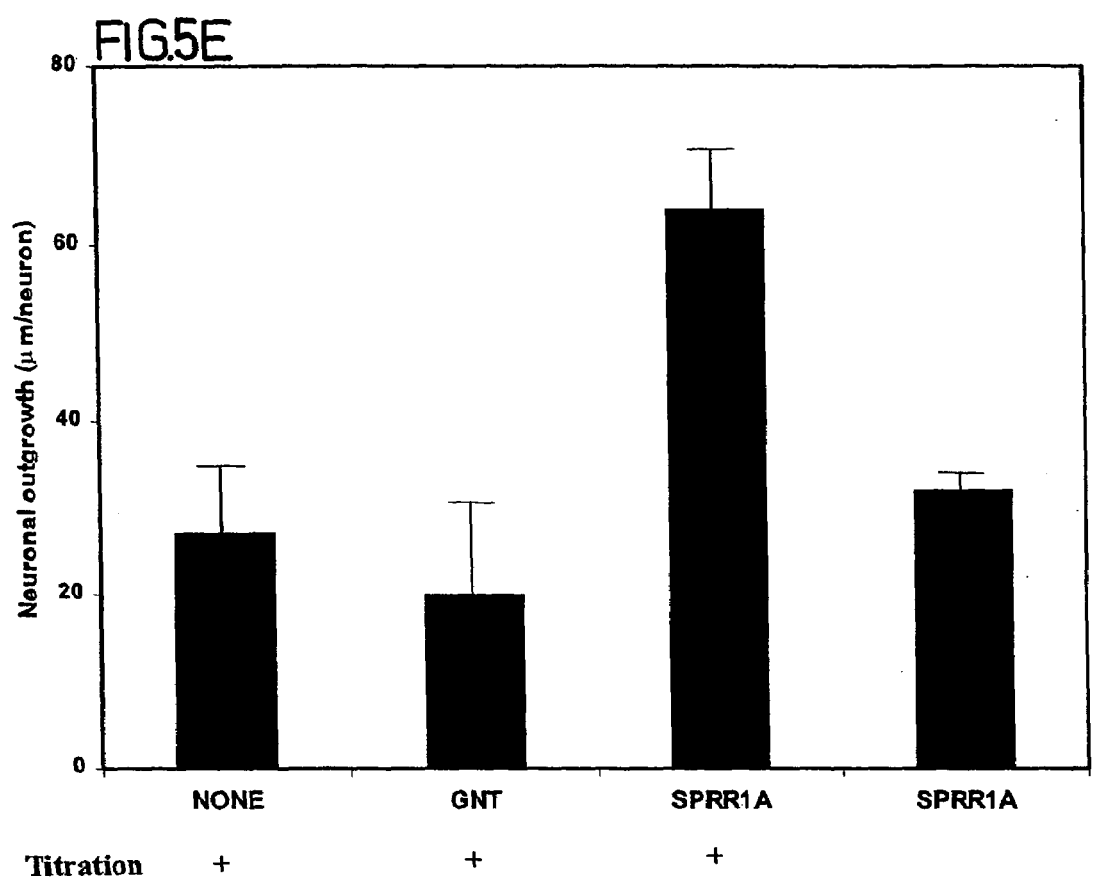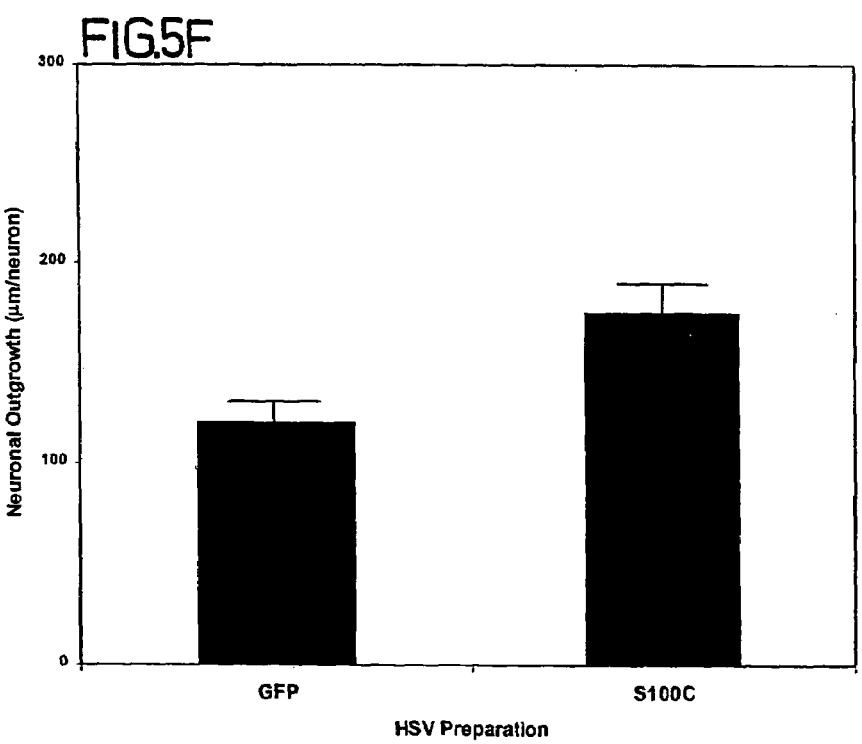

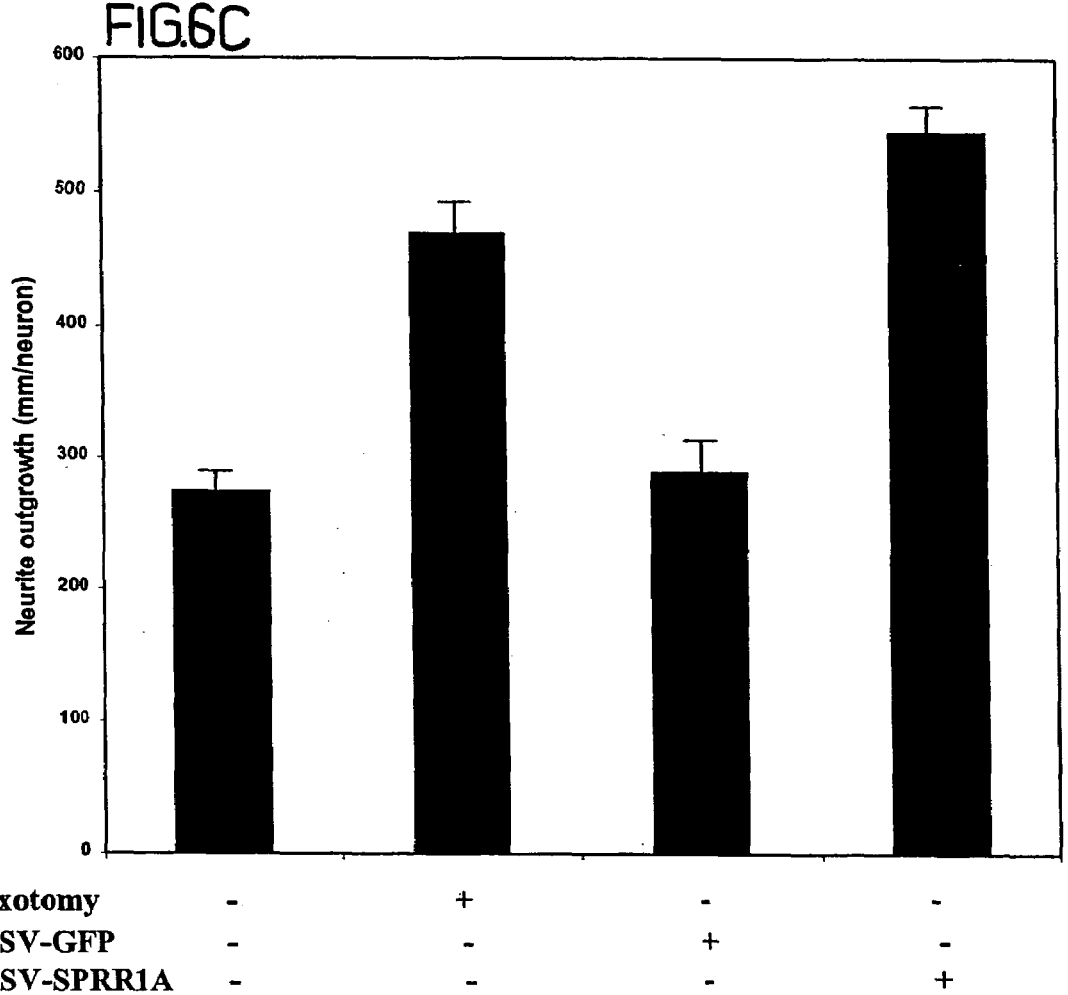

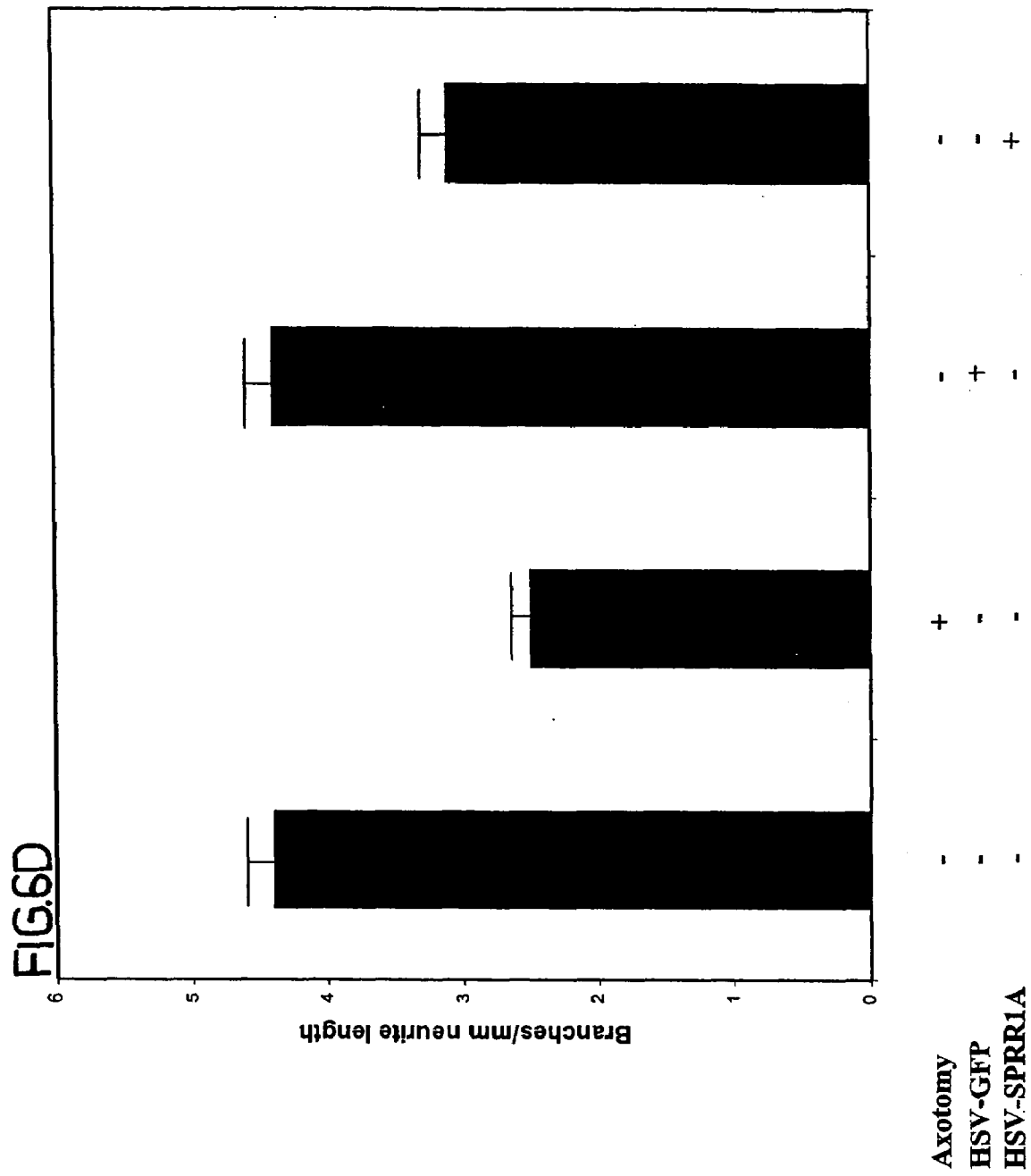

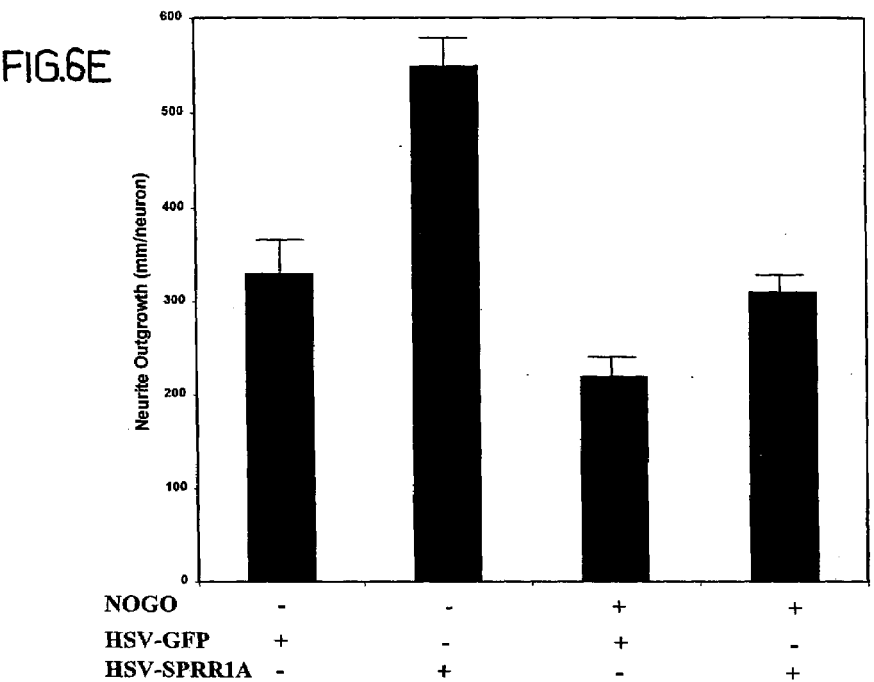
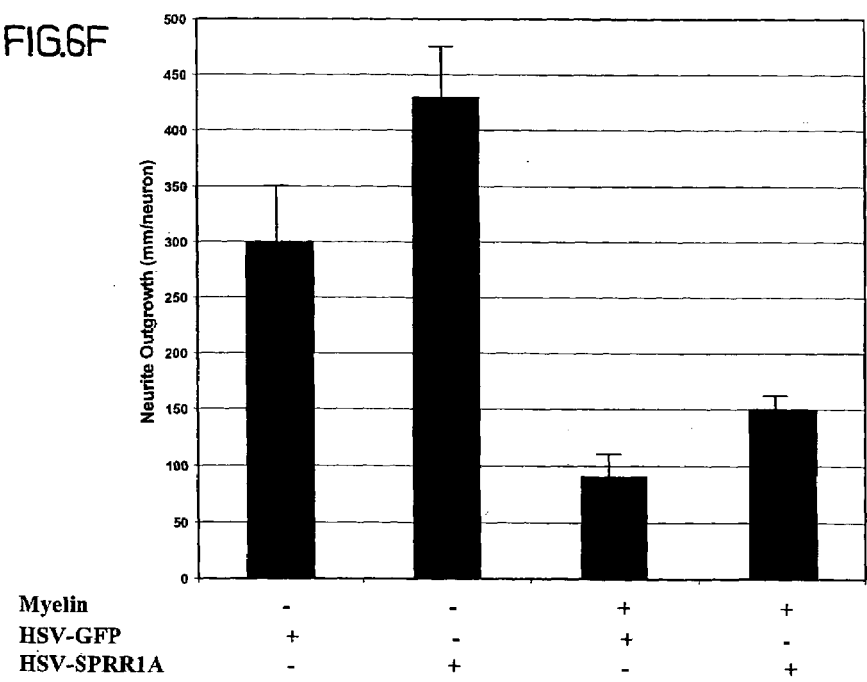

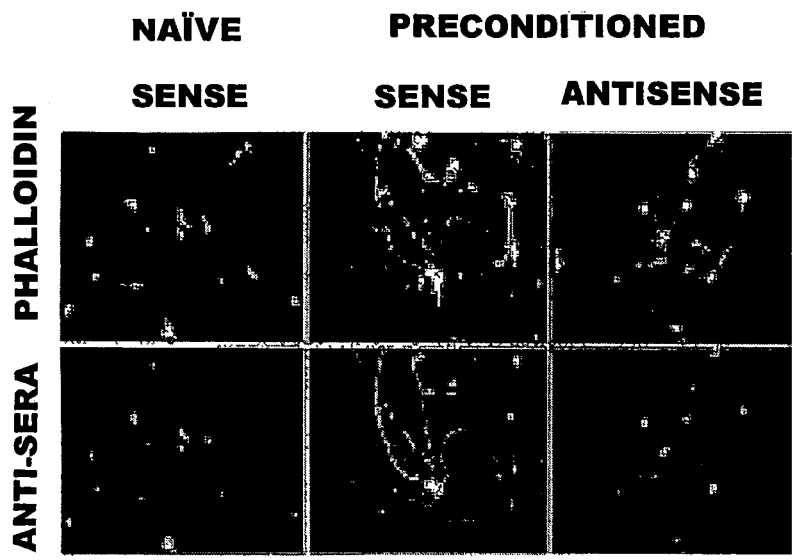
FIG. 7C
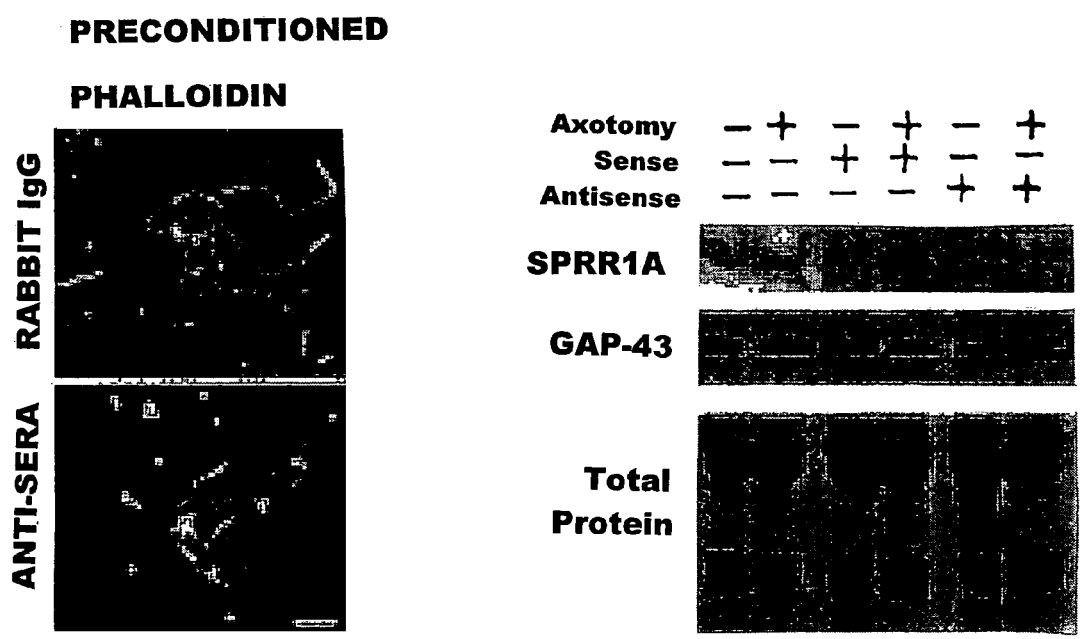
FIG. 7F
FIG. 7A

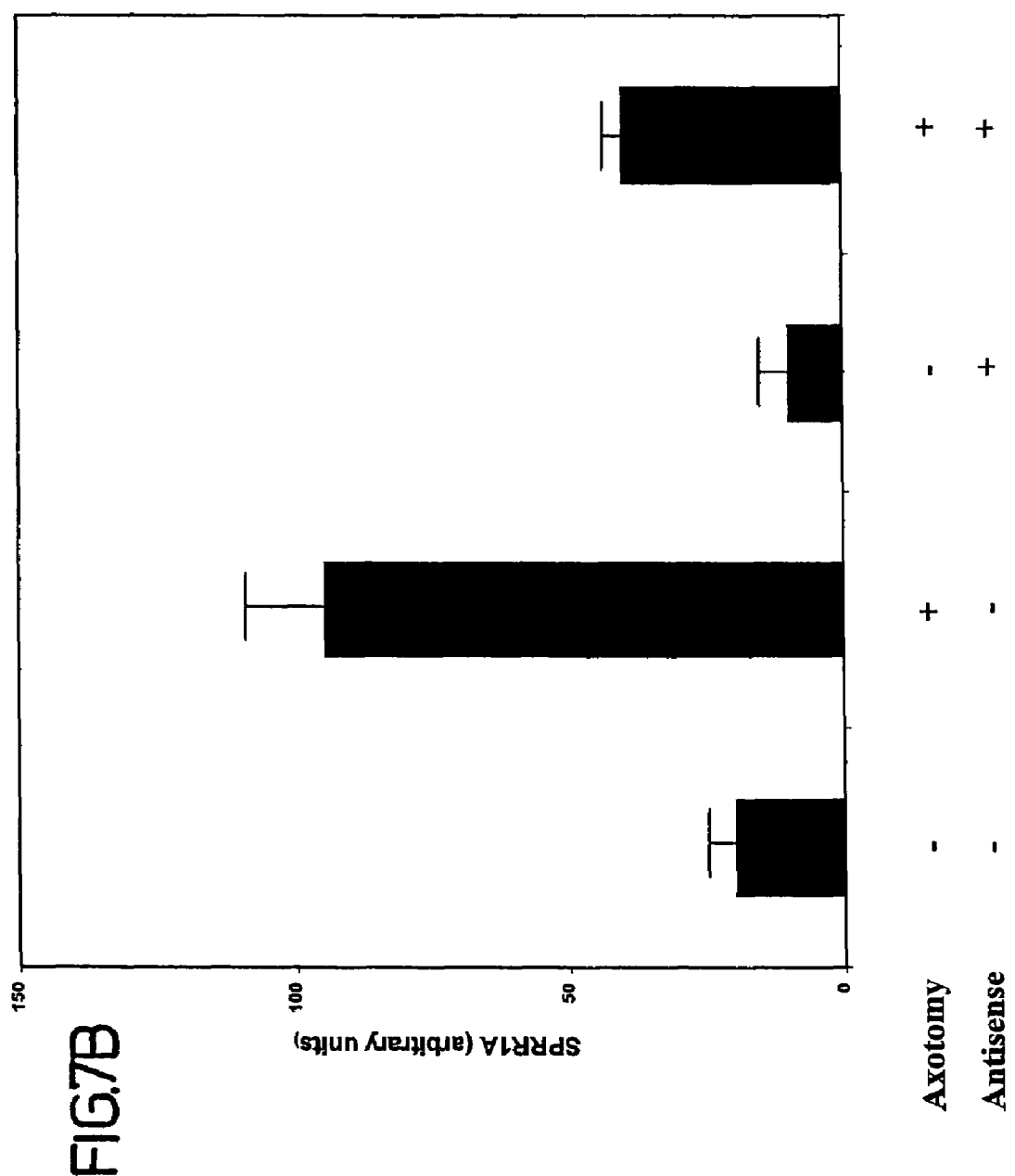

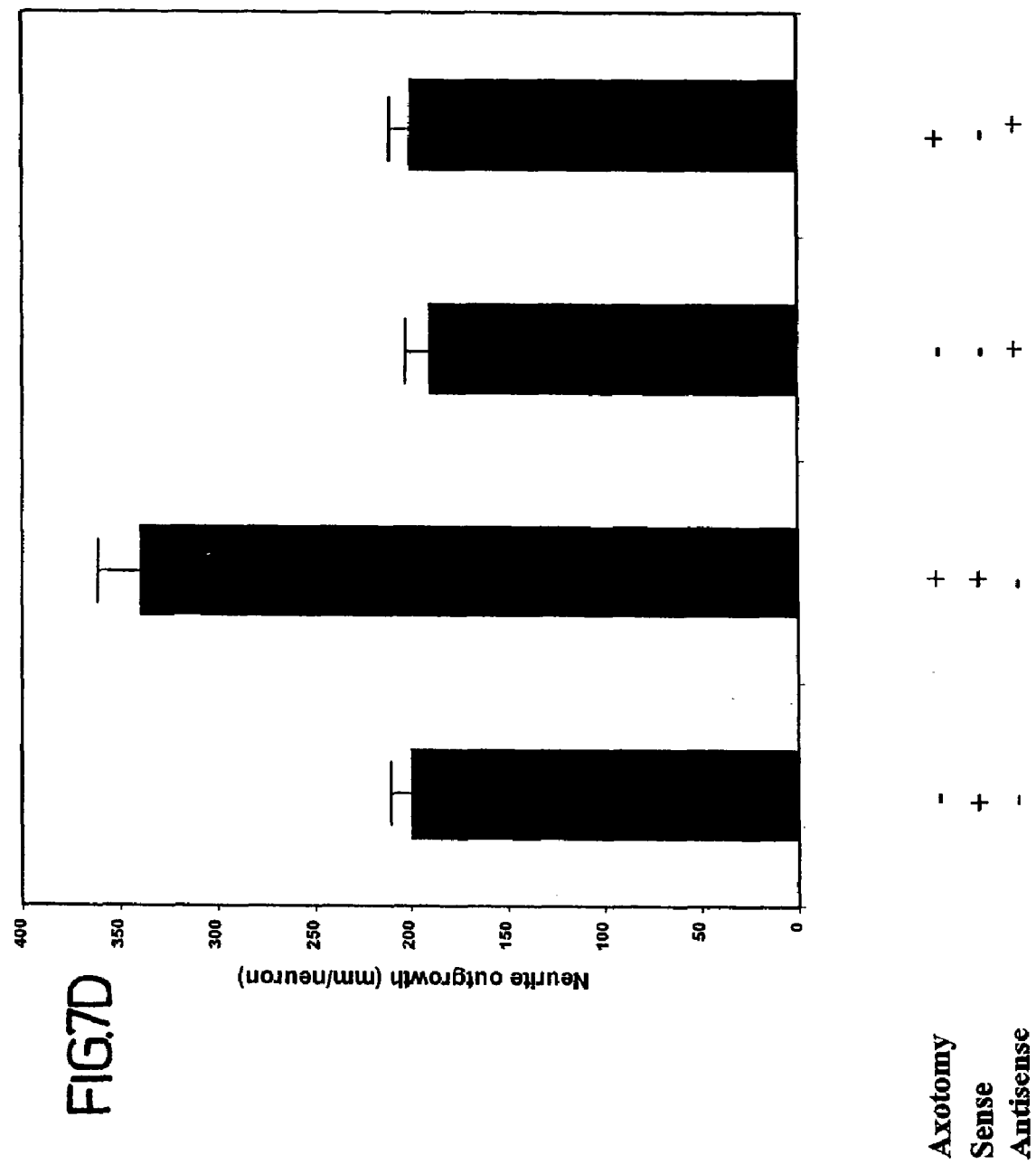

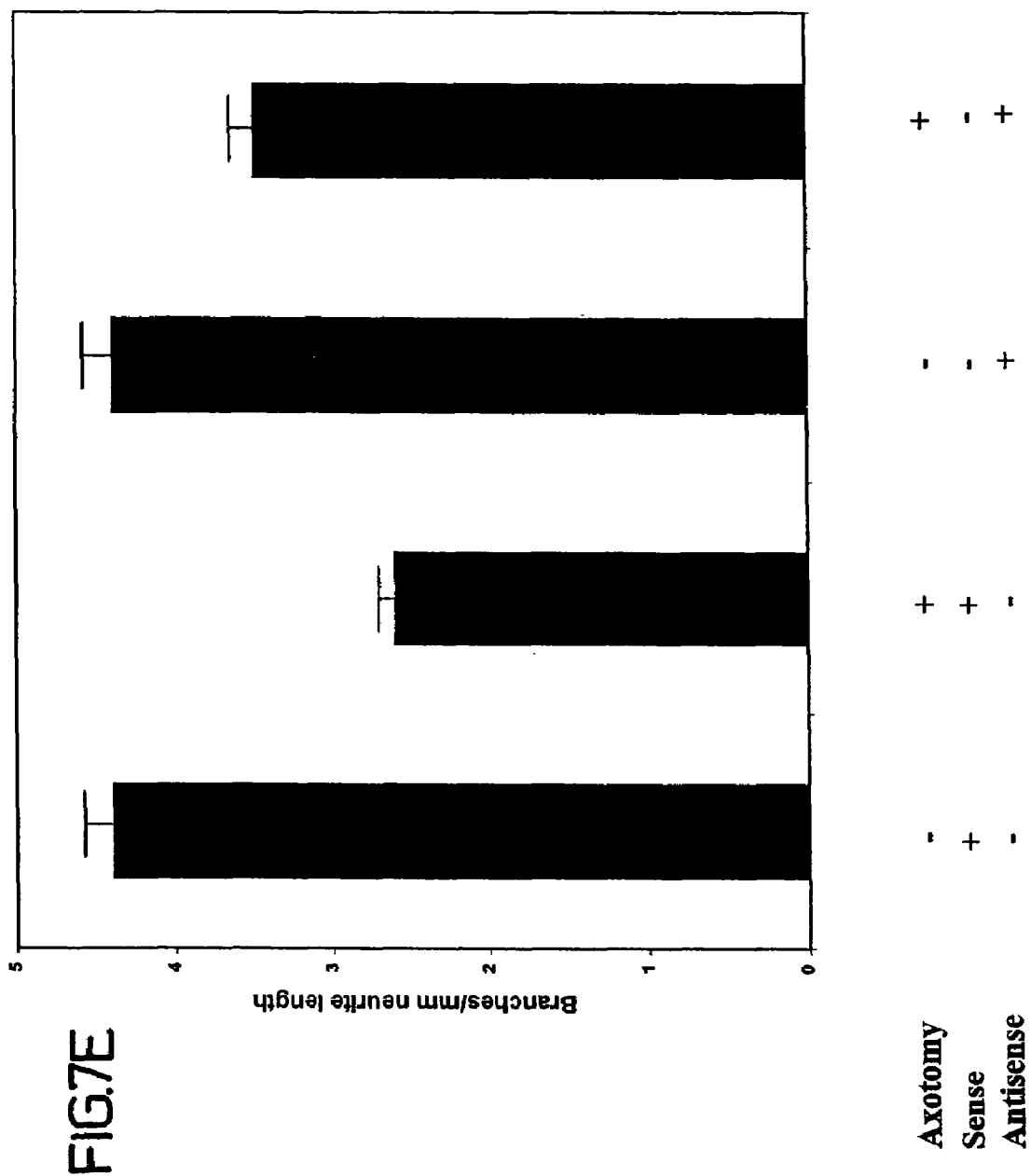

SPRR1A AND AXONAL REGENERATION

CROSS REFERENCE TO RELATED APPLICATIONS

This Application is a continuation of International Application No. PCT/US02/12564, filed Apr. 22, 2002, which claims priority to U.S. Provisional Patent Application No. 60/285,373, filed Apr. 21, 2001.

STATEMENT REGARDING FEDERALLY SPONSORED RESEARCH OR DEVELOPMENT

This invention was made in part using funds obtained from the U.S. Government (National Institutes of Health grants RO1 NS 93362 and F31 NS 11007) and the U.S. government may therefore have certain rights in this invention.

BACKGROUND OF THE INVENTION

The degree of axonal regeneration in the adult nervous system plays a major role in determining clinical outcomes in a range of neurologic conditions, from spinal cord injury to brain trauma to stroke to chronic progressive multiple sclerosis. In part, factors extrinsic to the neuron, such as Nogo, neurotrophins, and glial scar tissue, regulate the extent of axonal regeneration (Schnell et al., 1994; Fu and Gordon, 1997; Fawcett and Asher, 1999; Grand-Pre et al., 2000; Fournier and Strittmatter, 2001; Fournier et al., 2001). In addition, it is clear that different neurons respond in various ways to the same environment and that injury induces changes in the axonal growth capacity of an injured neuron. The "conditioning" nerve lesion studies of Woolf and colleagues (Chong et al., 1999; Neumann and Woolf, 1999) showed that peripheral axotomy, but not central axotomy, generates an enhanced axonal growth state. Presumably, this is attributable to the induction of neuronal regeneration-associated genes (RAG) by peripheral axotomy.

The injured PNS undergoes a stereotypical reaction to injury characterized by Wallerian degeneration in the distal portion of the nerve (Stoll et al., 1989) and a sprouting process at the proximal site. At the molecular level, there is evidence for a coordinated neuronal gene program involved in the repair process. Previous research has identified a few components of this molecular genetic switch to axon growth, although this is likely to be a very incomplete view (for review, see Fu and Gordon, 1997; Gillen et al., 1997). In general, RAGs are also highly expressed during nervous system development, suggesting that regeneration recapitulates development.

The majority of the identified RAGs encode proteins in one of several categories: cytoskeletal proteins, neurotransmitter metabolizing enzymes, neuropeptides, cytokines, neurotrophins, and neurotrophin receptors. In particular, the changes in cytoskeletal protein expression support the notion that developmental processes are being recruited. The general trend during both development and regeneration is to upregulate tubulin (Moskowitz and Oblinger, 1995) and downregulate neurofilament proteins (Muma et al., 1990; Troy et al., 1990; Wong and Oblinger, 1990). Because microtubules and neurofilaments are differentially regulated, classic neurotransmitter systems are downregulated after axotomy (for review, see Grafstein and McQuarrie, 1978; Gordon, 1983; Zigmond et al., 1996), whereas many neuropeptides are upregulated. Axotomy-induced neuropeptides include vasoactive intestinal peptide (Nielsch and Keen, 1989), galanin (Villar et al., 1989), and neuropeptide Y (Wakisaka et al., 1991). Neurotrophic factors and their receptors play critical roles during nervous system development, and in many cases expression is increased after nerve axotomy. Nerve growth factor (Ernfors et al., 1989), brain-derived neurotrophic factor and neurotrophin-3 (Schecterson and Bothwell, 1992; Kobayashi et al., 1996), acidic fibroblast growth factor (Elde et al., 1991), platelet-derived growth factor (Sasahara et al., 1991; Yeh et al., 1991), and neuregulin (Marchionni et al., 1993) are examples in this group.

Perhaps the prototypical example of a RAG is GAP-43. Skene and Willard (1981) originally discovered GAP-43 as a rapidly transported axonal protein that is highly induced after sciatic nerve injury. GAP-43 protein is localized primarily in the axonal growth cone and is expressed during brain development. Its induction by trauma is correlated with substantial functional recovery after axonal injury (Skene and Willard, 1981; Katz et al., 1985; Skene, 1989; Gispen et al., 1991). GAP-43 plus CAP-23 overexpression supports a degree of CNS axon regeneration (Bomze et al., 2001). Although GAP-43 was first identified in a two-dimensional protein electrophoresis analysis of sciatic nerve injury (Skene and Willard, 1981), other RAGs have been identified using differential display analysis (Kiryu et al., 1995; Su et al., 1997) and expressed-sequence-tag approaches (Tanabe et al., 1999).

The identification of factors responsible for regeneration of functional neurons is critical to correcting nerve damage and restoring function to patients suffering from all forms of nerve damage. In particular, those factors demonstrated to play the strongest or most significant role in such regeneration are critical to the understanding of neuronal repair. Accordingly, there is a long-felt need to identify and understand the primary factors of neuron regeneration.

BRIEF SUMMARY OF THE INVENTION

The invention includes a method of inducing growth of a neuron. The method comprises administering to the neuron a polypeptide encoded by an SPRR1A polynucleotide.

In one aspect, the method of inducing growth of a neuron comprises administering to the neuron an SPRR1A polypeptide, and in yet another aspect, the method of inducing growth of a neuron comprises administering to the neuron a polypeptide fragment of an SPRR1A polypeptide.

In one embodiment of the invention, the neuron induced to grow is a peripheral nervous system neuron of a mammal. In yet another embodiment of the invention, the neuron is a central nervous system neuron of a mammal.

In another embodiment of the invention, the neuron induced to grow has been damaged, and in yet another embodiment of the invention, the neuron has been axotomized.

In an aspect of the invention, the neuron growth comprises axonal outgrowth, and in another embodiment, the neuron growth comprises nerve regeneration.

In another aspect of the invention, the neuron induced to grow is in a mammal, and in a further aspect of the invention, the neuron is in a human.

In an embodiment of the invention, the method of inducing nerve regeneration of a damaged nerve comprises administering to the damaged nerve a polypeptide encoded by an SPRR1A gene. In yet another embodiment, the damaged nerve is a nerve of the central nervous system of a mammal. In another embodiment of the invention, the damaged nerve is a nerve of the peripheral nervous system of a mammal. In yet another embodiment, the damaged nerve is a sciatic nerve.

In one aspect of the invention, a method of inducing growth of a neuron comprises administering to the neuron a polypeptide encoded by an SPRR1A gene, wherein the expression of the polypeptide is effected within the neuron.

In an embodiment of the invention, a method of identifying a test compound that modulates the activity of an SPRR1A polypeptide comprises administering to a neuron the test compound in the presence of the polypeptide and assaying the level of growth of the neuron in the presence of the test compound compared with the level of growth of another identical neuron in the absence of the test compound but in the presence of the polypeptide, wherein a higher or lower level of growth of the neuron in the presence of the test compound compared with the level of growth of the other identical neuron in the absence of the test compound is an indication that the test compound modulates the activity of the polypeptide. In a further aspect of the invention, growth of the neuron is stimulated. In yet another aspect of the invention, growth of the neuron is inhibited.

One aspect of the invention provides a diagnostic kit to monitor regeneration of a neuron, wherein the kit comprises a polypeptide comprising the amino acid sequence of an SPRR1A polypeptide. In another aspect of the invention, the amino acid sequence is a fragment of an SPRR1A polypeptide.

Another aspect of the present invention provides for an SPRR1A-like compound capable of inducing growth of a neuron when administered to the neuron. In a further aspect of the invention, an SPRR1A-like compound is capable of inducing nerve regeneration of a damaged nerve when administered to the nerve.

BRIEF DESCRIPTION OF THE DRAWINGS

FIG. 5E is a graph depicting significant ($p \leq 0.05$, Student's twotailed t test) increase in neurite outgrowth (±SEM) in neurons triturated with purified SPRR1A. Control triturations have no effect on outgrowth. SPRR1A protein added to the culture medium without trituration does not alter outgrowth.

FIG. 5F is a graph depicting neurite outgrowth for neurons overexpressing EGFP and S100C via recombinant HSV infection. A significant ($p \leq 0.05$, Student's two-tailed t test) increase in outgrowth is observed for the HSV-S100C-infected neurons 24 hr after plating.

FIG. 6C is a graph depicting neurite outgrowth in naive and preconditioned adult mouse DRG neurons (phalloidin staining) and in neurons expressing EGFP (as a control) or SPRR1A via recombinant HSV infection. A significant ($p \leq 0.05$, Student's two-tailed t test) increase in outgrowth is observed in HSV-SPRR1A-infected cultures 24 hr after plating. Data are means ±SEM from three experiments.

FIG. 6D is a graph depicting axonal branching for naive and preconditioned neurons and for HSV-EGFP- and HSV-SPRR1A-infected DRGs. It was confirmed that preconditioning and HSV-SPRR1A infection significantly ($p \leq 0.05$, Student's two-tailed t test) decrease branching compared with naive neurons, and a parallel decrease was observed in HSV-SPRR1A-infected DRGs. Data are means ±SEM from three experiments.

FIG. 6E is a graph depicting neurite outgrowth for HSV-EGFP- and HSV-SPRR1A-infected E13 DRG neurons plated on laminin or GST-Nogo-66 as the substrate. HSV-SPRR1A-infected neurons exhibit increased outgrowth relative to HSV-EGFP-infected neurons ($p \leq 0.05$, Student's two-tailed t test) when plated on laminin (10 µg/ml) or on Nogo (34 ng/mm2). Data are means ±SEM from five experiments.

FIG. 6F is a graph depicting neurite outgrowth for HSV-EGFP- and HSV-SPRR1A-infected E13 DRG neurons plated on laminin or bovine CNS myelin as the substrate. HSV-SPRR1A-infected neurons show increased outgrowth compared with HSV-EGFP-infected neurons ($p \leq 0.05$, Student's two-tailed t test) when plated on laminin (10 µg/ml) or on CNS myelin (45 ng/mm2). Data are means ±SEM from five experiments.

FIG. 7A is a collection of immunoblots that demonstrates that SPRR1A loss of function decreases axonal regeneration in adult DRGs. Immunoblots for SPRR1A and GAP-43 protein from adult mouse DRG neurons are illustrated. Naive or preconditioned neurons were cultured with sense or antisense oligonucleotides, as indicated. A decrease in SPRR1A immunoreactivity but not in GAP-43 levels is observed after treatment with antisense oligonucleotide. Coomassie brilliant blue staining reveals that total protein levels are equal in all samples.

FIG. 7B is a graph that quantifies the SPRR1A signal from immunoblots of control and antisense-treated DRG cultures as described in FIG. 7A. The level of SPRR1A protein decreases to nearly basal levels in neurons treated with antisense oligonucleotide. Data are means ±SEM from three experiments.

FIG. 7C is a collection of images showing adult mouse DRG neurons in the naive or preconditioned state cultured with sense or antisense oligonucleotides. Each vertical pair of panels shows the same field double-labeled with phalloidin to reveal F-actin or with anti-SPRR1A. Naive neurons treated with sense oligonucleotides extend short, branched processes without SPRR1A protein, whereas preconditioned neurons display elongated, less branched axons expressing SPRR1A protein. Preconditioned neurons treated with antisense oligonucleotides exhibit little anti-SPRR1A staining and morphological features similar to those of naive neurons.

FIG. 7D is a graph depicting neurite outgrowth for naive and preconditioned neurons treated with either sense or antisense oligonucleotides. A significant ($p \leq 0.05$, Student's two-tailed t test) decrease in axonal length is observed for antisense oligonucleotide-treated preconditioned neurons compared with sense-treated preconditioned neurons. Data are means ±SEM from three experiments.

FIG. 7E is a graph depicting axonal branching for naive and preconditioned adult mouse DRG neurons treated with sense or antisense oligonucleotides. For naive neurons, oligonucleotide treatment did not alter branching. For preconditioned neurons, antisense oligonucleotide treatment increased branching compared with sense-treated neurons (p≦0.05, Student's two-tailed t test). Data are means ±SEM from three experiments.

DETAILED DESCRIPTION OF THE INVENTION

Figure 1A:
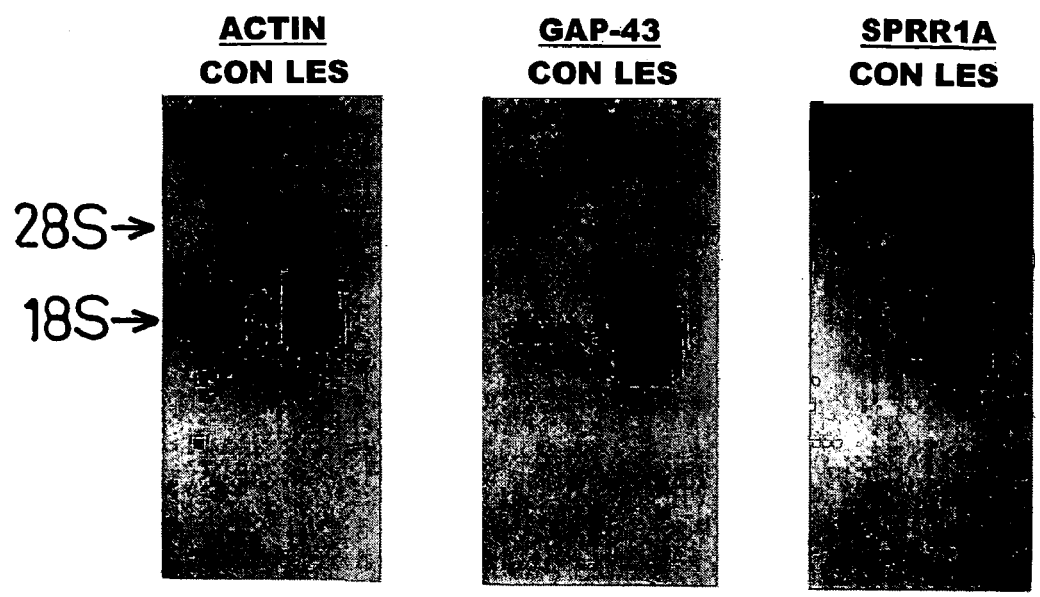
FIG. 1A is a series of Northern blots, revealing that actin mRNA levels remain constant in lumbar DRGs 1 week after sciatic nerve lesion (LES) compared with control (CON) levels. DRGs dramatically upregulate both sprr1a and gap-43 mRNA after sciatic nerve transection. Migration of 28S and 18S ribosomal RNA is shown at left.

The present invention includes nucleic acids, proteins, pharmaceutical compositions, and methods for the modulation of neuron growth and regeneration. A key feature of the invention, therefore, is to administer to a neuron a neuron growth-modulating composition. The importance of stimulating neuron growth and regeneration is well known in the art, as is the lack of a means by which to stimulate nerve growth and regeneration.

The present invention relates to a small proline-rich repeat protein, SPRR1A (Kartasova and van de Putte, 1988; Kartasova et al., 1988; Gibbs et al., 1993; Jin and Strittmatter, 1997; Fournier et al., 2001). In the present invention, SPRR1A is administered to a neuron to stimulate growth of the axon. In one key aspect of the invention, SPRR1A protein is administered to a damaged neuron to stimulate regeneration of the axon to form a complete, functional neuron.

In one aspect of the invention, there is provided an isolated nucleic acid encoding SPRR1A. The isolated nucleic acid of the present invention may be isolated from numerous sources, including mammalian tissue and cDNA libraries. The isolated nucleic acid may be characterized using any technique well-known in the art, such as nucleotide sequencing (Sambrook et al., 1989, Molecular Cloning: A Laboratory Manual, Cold Spring Harbor Laboratory, New York). Upon identification of the isolated nucleic acid as encoding a SPRR1A polypeptide having the biological activity of modulating axonal outgrowth of a neuron, the isolated nucleic acid may be modified as described herein.

SEQ ID NO:1 illustrates full-length *Mus musculus* (mouse) SPRR1A cDNA (GenBank accession number X91824), and the corresponding protein is set forth in SEQ ID NO:2. In one aspect of the invention, amino acid residues are truncated from the amino-terminal portion of SEQ ID NO:2 and amino acid residues are truncated from the carboxy-terminal portion of SEQ ID NO:2 to form a truncated SPRR1A protein.

In one aspect of the invention, a peptide derived from the full-length SPRR1A protein can exhibit the same active properties as the full-length SPRR1A protein set forth in SEQ ID NO:2. SEQ ID NO:3, HPKAPEPCNPKVPEPC-QPKVPEPC, is administered to a neuron to stimulate growth of the axon. In one key aspect of the invention, a peptide derived from SPRR1A is administered to a damaged neuron to stimulate regeneration of the axon to form a complete, functional neuron.

Modified gene sequences, i.e. genes having sequences that differ from the gene sequences encoding the naturally-occurring proteins, are also encompassed by the invention, so long as the modified gene still encodes a protein having the biological activity of modulating the growth of a neuron. These modified gene sequences include modifications caused by point mutations, modifications due to the degeneracy of the genetic code or naturally occurring allelic variants, and further modifications that have been introduced by genetic engineering, i.e., by the hand of man. Thus, the term nucleic acid also specifically includes nucleic acids composed of bases other than the five biologically occurring bases (adenine, guanine, thymine, cytosine and uracil).

In another aspect of the present invention, a nucleic acid encoding SPRR1A may have at least one nucleotide inserted into the naturally-occurring nucleic acid sequence. Alternatively, an additional SPRR1A may have at least one nucleotide deleted from the naturally-occurring nucleic acid sequence. Further, an SPRR1A of the invention may have both a nucleotide insertion and a nucleotide deletion present in a single nucleic acid sequence encoding the enzyme.

Techniques for introducing changes in nucleotide sequences that are designed to alter the functional properties of the encoded proteins or polypeptides are well known in the art. Such modifications include the deletion, insertion, or substitution of bases, and thus, changes in the amino acid sequence. As is known to one of skill in the art, nucleic acid insertions and/or deletions may be designed into the gene for numerous reasons, including, but not limited to modification of nucleic acid stability, modification of nucleic acid expression levels, modification of expressed polypeptide stability or half-life, modification of expressed polypeptide activity, modification of expressed polypeptide properties and characteristics, and changes in glycosylation pattern. All such modifications to the nucleotide sequences encoding such proteins are encompassed by this invention.

It is not intended that the present invention be limited by the nature of the nucleic acid employed. The target nucleic acid may be native or synthesized nucleic acid. The nucleic acid may be DNA or RNA and may exist in a double-stranded, single-stranded or partially double-stranded form. Furthermore, the nucleic acid may be found as part of a virus or other macromolecule. See, e.g., Fasbender et al., 1996, J. Biol. Chem. 272:6479-89.

The nucleic acids may be purified by any suitable means, as are well known in the art. For example, the nucleic acids can be purified by reverse phase or ion exchange HPLC, size exclusion chromatography or gel electrophoresis. Of course, the skilled artisan will recognize that the method of purification will depend in part on the size of the DNA to be purified.

An isolated polynucleotide of the present invention may be cloned into a DNA vector. A polynucleotide/vector construct can be used to facilitate large scale production of the polynucleotide of the invention or to express the polypeptide encoded by the polynucleotide of the invention. In another aspect of the invention, mouse sprr1A is cloned into an expression vector downstream of the 3' end of a sequence encoding multiple functional tags. The amino-terminal fusion to sprr1A may comprise a multiple-histidine sequence to aid in purification of the expressed polypeptide, an epitope to aid in detection of the polypeptide, or a protease cleavage site for cleavage of the purification and detection sequences from the expressed polypeptide.

In yet another aspect of the present invention, SPRR1A may be expressed in mammalian cells, using an appropriate expression vector and mammalian cell. However, as evidenced by the literature relevant to the art, one skilled in the art will appreciate that SPRR1A can also be expressed in other eukaryotic cells, including yeast, or prokaryotic cells, including bacteria. SPRR1A protein of the present invention may be expressed using any technique well-known in the art, such as simple expression, high level expression, or overexpression (Sambrook et al., 1989, Molecular Cloning: A Laboratory Manual, Cold Spring Harbor Laboratory, New York).

SEQ ID NO:2 illustrates the full-length mouse SPRR1A polypeptide. SEQ ID NO:3 illustrates a truncated form of SPRR1A of the present invention. The truncated form of SPRR1A has deleted amino acid sequence from the amino-terminus of the polypeptide and from the carboxy-terminus of the polypeptide.

The present invention also provides for analogs of proteins or peptides encoded by SPRR1A genes. Analogs can differ from naturally occurring proteins or peptides by conservative amino acid sequence differences or by modifications which do not affect sequence, or by both.

For example, conservative amino acid changes may be made, which although they alter the primary sequence of the protein or peptide, do not normally alter its function. Conservative amino acid substitutions typically include substitutions within the following groups:

glycine, alanine;
valine, isoleucine, leucine;
aspartic acid, glutamic acid;
asparagine, glutamine;
serine, threonine;
lysine, arginine;
phenylalanine, tyrosine.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

In another aspect of the present invention, compositions comprising an isolated SPRR1A protein may include highly purified SPRR1A protein. Substantially pure protein isolated and obtained as described herein may be purified by following known procedures for protein purification, wherein an immunological, enzymatic or other assay is used to monitor purification at each stage in the procedure. Protein purification methods are well known in the art, and are described, for example in Deutscher et al. (ed., 1990, Guide to Protein Purification, Harcourt Brace Jovanovich, San Diego).

The present invention is also useful for diagnostic assays. The diagnostic assays offer a process for diagnosing or determining the state of regeneration of a neuron. Such information may be diagnosed by methods comprising determining from a sample derived from a subject an abnormally decreased or increased level of polypeptide or mRNA. Decreased or increased expression can be measured at the RNA level using any of the methods well known in the art for the quantitation of polynucleotides, such as, for example, nucleic acid amplification, for instance PCR, RT-PCR, RNase protection, Northern blotting and other hybridization methods. Assay techniques that can be used to determine levels of a protein, such as a polypeptide of the present invention, in a sample derived from a host are well-known to those of skill in the art. Such assay methods include radioimmunoassays, competitive-binding assays, Western Blot analysis and ELISA assays.

Thus in another aspect, the present invention relates to a diagnostic kit which comprises:

(a) a polynucleotide of the present invention, preferably the nucleotide sequence of SEQ ID NO:1, or a fragment thereof; or (b) a nucleotide sequence complementary to that of (a); or (c) a polypeptide of the present invention, preferably the polypeptide of SEQ ID NO:2, SEQ ID NO:3, or fragments thereof, or (d) an antibody to a polypeptide of the present invention, preferably to the polypeptide of SEQ ID NO:2.

It will be appreciated that in any such kit, (a), (b), (c) or (d) also comprises an instructional material for use thereof. Such a kit will be of use in diagnosing the state of regeneration of a neuron.

As used herein, an "instructional material" includes a publication, a recording, a diagram, or any other medium of expression which can be used to communicate the usefulness of the composition of the invention for its designated use. The instructional material of the kit of the invention may, for example, be affixed to a container which contains the composition or be shipped together with a container which contains the composition. Alternatively, the instructional material may be shipped separately from the container with the intention that the instructional material and the composition be used cooperatively by the recipient.

In the present invention, just as SEQ ID NO:3 is a functional derivative of SEQ ID NO:2, a smaller part of SEQ ID NO:3 can be useful in the same applications as SEQ ID NO:3. Further, a non-peptide mimic of either SEQ ID NO:3 or a part of SEQ ID NO:3 can be readily prepared by one of ordinary skill in the art.

Disclosed herein is a method for the production of mouse SPRR1A by expressing the isolated gene encoding this enzyme in bacterial cells and subsequently using the protein to stimulate axonal growth in neurons. SPRR1A increases axonal outgrowth in both adult and embryonic neurons, and also increases axonal outgrowth of embryonic neurons on outgrowth-inhibitory substrates.

The present invention offers a method for regrowth and regeneration of the axonal portion of a damaged neuron. Expression and/or upregulation of SPRR1A protein in an embryonic neuron directly promotes axonal outgrowth. Further, expression and/or upregulation of SPRR1A protein in a neuron increases axonal outgrowth and promotes the "branching-to-elongating" morphological switch akin to regeneration in adult neurons.

Definitions

The articles "a" and "an" are used herein to refer to one or to more than one (i.e. to at least one) of the grammatical object of the article. By way of example, "an element" means one element or more than one element.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g, as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

A "polynucleotide" means a single strand or parallel and anti-parallel strands of a nucleic acid. Thus, a polynucleotide may be either a single-stranded or a double-stranded nucleic acid.

The term "nucleic acid" typically refers to large polynucleotides.

The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

"Neuron" refers to a nerve cell, comprised generally of a body in which the nucleus resides, dendrites, and an axon for transport of the nerve impulse.

"Nerve damage" refers to any deliberate or accidental physical injury to at least one neuron resulting in an alteration of the normal function or physical structure of the neuron.

"Growth of a neuron" refers to the original biological development of an embryonic neuron, the continued development of a young neuron, the regeneration of any part of a damaged neuron, or any change in size, shape, or structure of a viable neuron. As it is used in the present application, neuron growth encompasses development of the body, dendrites, and axon of a neuron.

"Axonal outgrowth" is the development and physical extension of an axon outwardly from the body of the neuron.

"Nerve regeneration" refers to the process in which at least one damaged neuron undergoes physical and chemical changes that result in the neuron once again becoming structurally and functionally identical to a normal, healthy neuron.

"Stimulation of neuronal growth" refers to an increase in the rate or degree of the original biological development of an embryonic neuron, the continued development of a young neuron, the regeneration of any part of a damaged neuron, or any change in size, shape, or structure of a viable neuron.

"Inhibition of neuronal growth" refers to a decrease in the rate or degree of the original biological development of an embryonic neuron, the continued development of a young neuron, the regeneration of any part of a damaged neuron, or any change in size, shape, or structure of a viable neuron.

"Modulation of neuronal growth" refers to either an increase or a decrease in the rate or degree of the original biological development of an embryonic neuron, the continued development of a young neuron, the regeneration of any part of a damaged neuron, or any change in size, shape, or structure of a viable neuron.

"Modulation of activity of a polypeptide" refers to an increase or a decrease in the rate or degree of biological activity of the polypeptide, an increase or a decrease in the affinity of the polypeptide for a target, an increase or a decrease in the expression levels of the polypeptide, or an increase or a decrease in the biological effect mediated by the polypeptide.

The "peripheral nervous system" is the network of nerves in a mammal that connects the brain and spinal cord to the rest of the body.

The "central nervous system" in a mammal is comprised of the brain and spinal cord.

The "sciatic nerve" is the large, main nerve to the leg of a mammal, running from the lower spinal cord to the bottom of the leg.

An "SPRR1A-like compound" is any small molecule chemical compound that mimics the structure or function of SPRR1A.

A "small-molecule mimic" of SPRR1A is a chemical compound of lower molecular weight than SPRR1A. A small-molecule mimic of SPRR1A has similar structural and/or charge distribution properties to SPRR1A, and it may or may not be a proteinacious compound. By nature of its similarity to at least a portion of SPRR1A, the small-molecule SPRR1A mimic will have one or more of the same biological properties as SPRR1A.

A "test compound" is a non-SPRR1A molecule that has the ability to modulate the growth of a neuron in the presence of SPRR1A.

Compounds which are identified using any of the methods described herein may be formulated and administered to a mammal for treatment of the diseases disclosed herein are now described.

The invention encompasses the preparation and use of pharmaceutical compositions comprising a compound useful for treatment of the diseases disclosed herein as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs, birds including commercially relevant birds such as chickens, ducks, geese, and turkeys.

Pharmaceutical compositions that are useful in the methods of the invention may be prepared, packaged, or sold in formulations suitable for oral, rectal, vaginal, parenteral, topical, pulmonary, intranasal, buccal, ophthalmic, intrathecal or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyamide and cyanate scavengers.

Controlled- or sustained-release formulations of a pharmaceutical composition of the invention may be made using conventional technology.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Typically dosages of the compound of the invention which may be administered to an animal, preferably a human, range in amount from 1 μg to about 100 g per kilogram of body weight of the animal. While the precise dosage administered will vary depending upon any number of factors, including but not limited to, the type of animal and type of disease state being treated, the age of the animal and the route of administration. Preferably, the dosage of the compound will vary from about 1 mg to about 10 g per kilogram of body weight of the animal. More preferably, the dosage will vary from about 10 mg to about 1 g per kilogram of body weight of the animal.

The compound may be administered to an animal as frequently as several times daily, or it may be administered less frequently, such as once a day, once a week, once every two weeks, once a month, or even lees frequently, such as once every several months or even once a year or less. The frequency of the dose will be readily apparent to the skilled artisan and will depend upon any number of factors, such as, but not limited to, the type and severity of the disease being treated, the type and age of the animal, etc.

A test compound is a non-SPRR1A molecule that has the ability to modulate the growth of a neuron in the presence of SPRR1A. A test compound may be identified by administering to a neuron the test compound in the presence of the polypeptide and assaying the level of growth of the neuron in the presence of the test compound compared with the level of growth of another identical neuron in the absence of the test compound but in the presence of the polypeptide, wherein a higher or lower level of growth of the neuron in the presence of the test compound compared with the level of growth of the other identical neuron in the absence of the test compound is an indication that the test compound modulates the activity of the polypeptide.

A test compound identified by this method may be used as part of a therapeutic composition to be administered to a patient, wherein the administration of the therapeutic composition modulates neuron growth in the patient.

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein. The Materials and Methods used in the experiments presented in the invention are now described.

Surgery and harvesting of mRNA. Adult male C57BL/6 mice were anesthetized by intraperitoneal injection of avertin. The sciatic nerve at the midthigh level was either completely transected or crushed by compression with Dumont No. 5 forceps for 30 sec. For retrograde labeling with Fluoro-Gold (Molecular Probes, Eugene, Oreg.), the transected axons were exposed to 1 μl of 1 mg/ml Fluoro-Gold at the time of the transection. Animals were killed 1 week after injury, and the ipsilateral DRGs from L3, L4, and L5 were removed into liquid nitrogen. Contralateral DRGs served as control samples. Poly(A)-positive RNA was harvested from DRGs using the Micro-Fast Track 2.0 mRNA Isolation Kit (Invitrogen, Carlsbad, Calif.), or total RNA was extracted with an RNA easy mini kit (Qiagen, Valencia, Calif.).

In spinal cord injury studies, mice were anesthetized with ketamine/xylazine, and the spinal cord was exposed through T10 laminectomies. The spinal cord was completely transected, and 1 μl of 1 mg/ml Fluoro-Gold solution was applied at the lesion site. The surgical site was closed, and animals were processed for biochemical or histological analysis after a 1 week survival period. Control DRG samples were taken from cervical levels and axotomized samples were taken from lumbar levels.

Microarray analysis. The mRNA from control and lesion DRG samples was reverse-transcribed in the presence of Cy3-dUTP and Cy5-dUTP to generate two distinct hybridization probes. These probes were hybridized to a cDNA microarray consisting of sequence-verified amplified PCR products selected from a Unigene mouse cDNA set spotted onto a glass matrix (Mouse GEM1, details at www.incyte.com). The normalized ratio of hybridization signal between samples to the arrayed cDNA is reported.

Northern blot analysis. Northern blots were performed as described previously (Goshima et al., 1995) using 400 ng of Poly(A+) RNA or 2 μg of total RNA from control and lesion DRG samples. Gene-specific $^{32}$P-labeled probes were synthesized by random priming and hybridized to membranes at 42° C. in 10% dextran sulfate, 50% formamide, 5× standard saline phosphate/EDTA (0.18 M NaCl, 10 mM phosphate, pH 7.4, 1 mM EDTA), and 1% SDS. After the membranes had been washed at 42° C. in 2×SSC and 1% SDS, autoradiographs were generated.

Immunologic procedures. The SPRR1A cDNA (X91824) was subcloned into pTrc-His (Invitrogen). Recombinant SPRR1A protein with an N terminal His-6 tag was purified from transformed Escherichia coli on a nickel resin. Rabbits were immunized with SPRR1A-His protein. Antiserum was diluted 1:1000 for immunohistology and 1:3000 for immunoblots. Immunologic controls included preimmune serum and blockade with protein antigen. SPRR1A protein levels on immunoblots were quantified from densitometric analysis of standard curves of purified recombinant SPRR1A protein processed in parallel.

The S100C cDNA (AA253928) was subcloned into the pGEX2T vector, and glutathione S-transferase (GST)-S100C was purified from transformed E. coli using glutathione Sepharose. Rabbits were immunized with the GST-S100C protein, and antiserum was diluted to 1:100 for immunohistochemistry and immunoblotting.

One week after sciatic nerve transection or thoracic spinal cord transection [sciatic nerve injury (SCI)], mice were killed and perfused with 4% paraformaldehyde. DRGs ipsilateral (lesion) and contralateral (control) to the transected nerve or DRGs above (control) or below (lesion) the SCI were dissected, post-fixed, and frozen in embedding medium. The tissue was cryosectioned at 10-20 μm and stained with anti-SPRR1A or anti-S100C antisera.

In situ hybridization. mRNA was localized in DRG sections by the digoxigenin-labeled riboprobe method (Wilkinson and Nieto, 1993; Goshima et al., 1995). Full-length antisense probes were used, and sense probes produced no signal.

COS-7 cell transfections. The full-length mouse SPRR1A (X91824) and S100C (AA253928) cDNAs were transferred into pCDNA3.1 (Invitrogen) such that the vector encoded C-terminal Myc-tagged SPRR1A and C-terminal Myc-His-tagged S100C. COS-7 cells were transfected with pCDNA3.1-SPRR1A-Myc or pCDNA3.1-S100C-Myc-His or cotransfected with both plasmids using the Fugene method (Boehringer Mannheim, Indianapolis, Ind.). The cells were fixed with 4% paraformaldehyde/20% sucrose after 36 hr of transfection and stained with appropriate combinations of anti-SPRR1A (1:1000), anti-S100C (1:100), mouse monoclonal anti-His (C terminus) (1:500) (Invitrogen), rhodamine-phalloidin (1 U/ml) (Molecular Probes), FITC-anti-rabbit IgG (1:200) (Sigma, St. Louis, Mo.), or tetramethylrhodamine isothiocyanate-anti-mouse IgG (1:200) (Sigma). Cells were examined with a Zeiss LSM-510 confocal microscope (Zeiss, Thornwood, N.Y.).

Actin cosedimentation assay. The actin cosedimentation protocol has been described previously (Gonzalez et al., 1998; Sakaguchi et al., 2000). Purified monomeric actin (G-actin, 25 μM; Cytoskeleton, Denver, Colo.) was incubated with recombinant SPRR1A (200 nM), GST-S100C (2 μM), or GST (2 μM) in an actin polymerization buffer (5 mM Tris, pH 8.0, 1.0 mM CaCl2, 1.0 mM DTT, 0.2 mM ATP, 100 mM KCl, 2.0 mM MgCl2) at room temperature for 60 min. Polymerized actin was sedimented by centrifugation at 100,000 μg for 1 hr. Equal volumes of the particulate and supernatant fractions were analyzed by SDS-PAGE and immunoblotting.

Herpes simplex virus preparation and protein trituration. The coding region of mouse SPRR1A was amplified by PCR with an in-frame C-terminal Myc epitope and ligated to the pHSVprPUC vector. Similarly, the S100C coding region with a Myc tag was ligated to pHSVprPUC vector. The resulting plasmids were transfected into 2-2 cells with Fugene and then superinfected with 5 dl 1.2 herpes simplex virus (HSV) helper virus 1 d later as described previously (Nakamura et al., 1998; Takahashi et al., 1998, 1999). Recombinant virus was amplified through three passages and stored at −80° C. Freshly dissociated DRG neurons were allowed to adhere to cultured dishes for 30 min and then incubated with HSV preparations encoding for SPRR1A, S100C, enhanced green fluorescent protein (EGFP), or Nogo receptor. Recombinant SPRR1A and S100C protein were triturated into dissociated DRGs by repetitive pipetting in the presence of 1 mg/ml of protein as described previously (Jin and Strittmatter, 1997).

DRG cultures and neurite outgrowth analysis. Embryonic day 7 (E7) chick, embryonic day 13 chick, or adult mouse DRGs were dissected and dissociated with 0.25% trypsin for 15 min at 37° C. For adult mouse DRG preparations, preincubation with 1 mg/ml collagenase was included. For preconditioned adult mouse DRG cultures, sciatic nerve lesions were performed 4 d before death and L3-L5 DRG dissection. Dissociated cells were preplated on tissue culture-treated plastic dishes for 1 hr at 37° C. Non-adherent cells (predominantly neurons) were collected and plated on plastic chamber slides coated with poly-L-lysine (100 μg)/laminin (10 μg/ml). In some cases, the substrate was coated with 45 ng/mm$^2$ bovine CNS myelin or 34 ng/mm$^2$ purified GST-Nogo-66 protein as described previously (Jin and Strittmatter, 1997; GrandPre et al., 2000; Fournier et al., 2001). After 6-36 hr, cells were fixed and stained, and neurite outgrowth was quantified. Images of each culture were captured with Olympix Software and analyzed with Scion Image (Jin and Strittmatter, 1997; GrandPre et al., 2000; Fournier et al., 2001). The total neurite length for each neuron was determined for 50-100 neurons in each experiment. The total number of branch points was divided by the total neurite length to obtain a branching index.

Antisense experiment. Phosphorothioate sense and antisense oligonucleotides spanning the translation initiation site (italic type) of the mouse sprr1a sequence (sense, p-thio-ATCTAACCATGAGTTCCCAC (SEQ ID NO:4); antisense, p-thio-GTGGGAACTCATGGTTAGAT (SEQ ID NO:5)) were generated. Adult mouse DRG cultures were incubated with purified oligonucleotides at concentrations of 10-50 μM. Immunoblot and immunohistological analysis was performed after 36 hr of culture.

Antibody blockade. Affinity-purified rabbit α-SPRR1A antibody (0.2 mg/ml) was triturated into DRG neurons before plating as described for other proteins (Jin and Strittmatter, 1997). Rabbit IgG (0.2 mg/ml) was used as a control. Triturated DRG neurons were cultured for 6 hr and then analyzed by immunohistochemistry and morphometry.

The results of the experiments presented in the invention are now described.

Microarray expression profile of axonal regeneration. An array containing 8500 cDNA species (Incyte mouse GEM) was used to analyze mRNA expression in the lumbar DRG 1 week after sciatic nerve transection. Sixteen mRNAs with greater than twofold upregulation or downregulation were detected. Eight of these transcripts were recognized previously as being induced or repressed by nerve regeneration, including galanin, neuropeptide Y, neurofilament, glial cell line-derived neurotrophic factor (GDNF) receptor α-subunit, pituitary adenylate cyclase-activating polypeptide, GTP-binding protein TC10, calcium channel α-2-δ subunit, and trkA receptor (Table 1). The results support the validity and sensitivity of this method. The eight other regulated genes include six known genes that were not recognized previously as being differentially regulated by axotomy and two novel genes.

Among the six known genes that were not recognized previously as being differentially regulated by axotomy, there were three genes sharing many common characteristics. SPRR1A, S100C, and p21/wild-type p53-activated factor 1 (WAF1) are all upregulated after UV irradiation of epithelial cells (Rosen et al., 1995). SPRR1A and S100C are induced during epithelial differentiation and are covalently cross-linked in the cornified envelope (CE) of terminally differentiated keratinocytes. Cross-linked SPRR1A and S100C are thought to contribute to the permeability barrier function of the CE. The common properties of these gene products, along with their concerted upregulation after sciatic nerve injury, raise the possibility that peripheral axonal regeneration uses a gene program shared with epithelial differentiation, making these genes of particular interest.

Figure 1B:
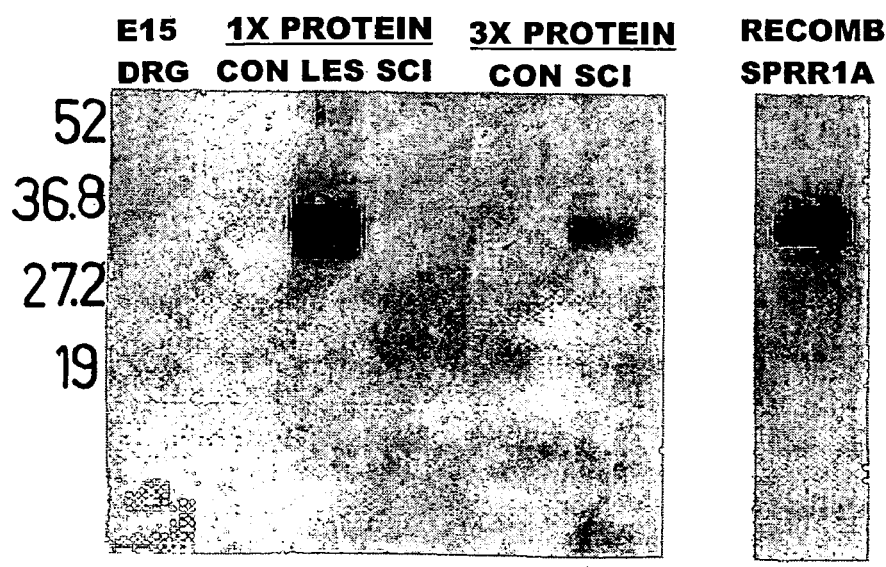
FIG. 1B is a pair of immunoblots for SPRR1A protein, demonstrating upregulation in adult L3-L5 DRGs (1×, 10 μg total protein; 3×, 30 μg total protein) after transection of the ipsilateral sciatic nerve (LES) compared with unlesioned (CON) samples. SPRR1A is not detected in uninjured E15 DRG samples. There is a small but detectable increase in SPRR1A protein after thoracic SCI seen only in the 3× samples. Molecular weight markers are shown at left.

SPRR1A is dramatically increased after sciatic nerve transection. The transcript that showed the highest level of upregulation was sprr1a (≧13-fold by microarray) (FIG. 1A). sprr1a is a member of the small, proline-rich family of genes composed of two sprr1 genes, eight sprr2 genes, and one sprr3 gene. At the core of the SPRR1A protein is a repeating XPKXPEPC (SEQ ID NO:6) octapeptide sequence. SPRR1A expression after axotomy was unexpected, because neuronal expression of the protein has not been detected previously. Indeed, SPRR1A has been considered a highly specific marker for the differentiation of keratinocytes and squamous epithelial cells (Kartasova and van de Putte, 1988; Kartasova et al., 1988; Gibbs et al., 1993). The increased expression of sprr1a detected by microarray analysis was verified by Northern blotting (FIG. 1A). sprr1a mRNA levels, like gap-43 levels, are greatly increased in the axotomized DRG sample compared with the control, whereas actin levels remain constant. As opposed to gap-43, no sprr1a mRNA is detectable in DRGs before axotomy. SPRR1A protein levels parallel mRNA levels in lumbar DRG extracts after sciatic nerve injury (FIG. 1B). As described previously (Kartasova and van de Putte, 1988; Kartasova et al., 1988), the 18 kDa SPRR1A protein migrates anomalously in SDS-PAGE at 34 kDa (FIG. 1B). This is most likely because of its unusual amino acid composition, consisting of 30% proline residues. Known RAGs, such as GAP-43, are expressed strongly during the axonal outgrowth period of embryonic development (Fu and Gordon, 1997; Gillen et al., 1997). No SPRR1A protein is observed, however, in E15 DRGs (FIG. 1B) or in E12 to postnatal day 4 samples. In this regard, SPRR1A is unique among known RAGs.

The upregulation of SPRR1A in DRG neurons after peripheral axotomy raised the question of whether these neurons would react in the same manner after a lesion of their central process. To assess this question, lumbar DRGs were removed from mice 1 week after thoracic SCI, and SPRR1A protein levels were analyzed. This lesion severs the central axon of those DRG neurons contributing to the dorsal columns, a significant subset of the lumbar DRG population. The SPRR1A protein increase after central axotomy is much less robust than that observed after peripheral axotomy and is undetectable unless the gels are overloaded with protein (FIG. 1B). The limited induction with central injury resembles the pattern with GAP-43 (Kalil and Skene, 1986) and might contribute to the cause of poor CNS axon regeneration.

Figure 1C:
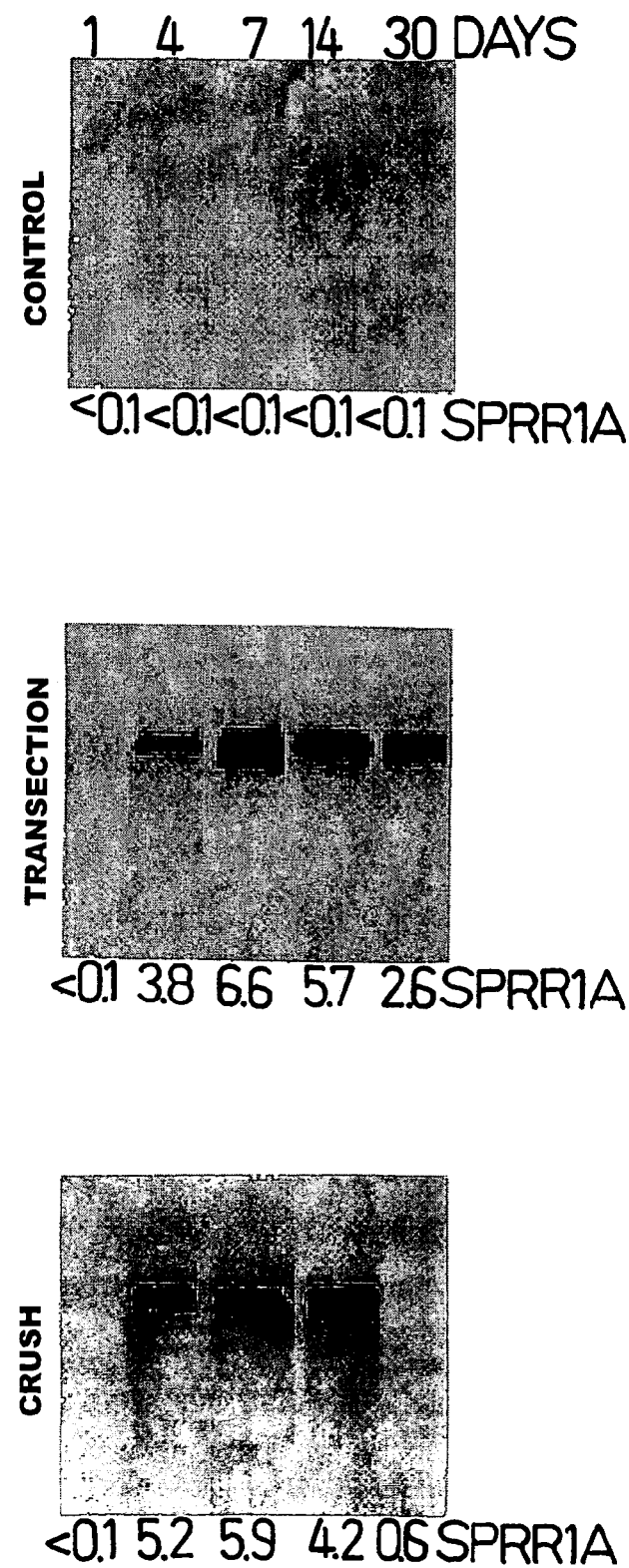
FIG. 1C is a collection of immunoblots demonstrating that DRGs contralateral to sciatic nerve axotomy do not express detectable SPRR1A by immunoblot (CONTROL, top). Nerve transection induces SPRR1A upregulation within 4 d after injury (middle). SPRR1A protein levels peak at 7-14 d, with a reduction 1 month after the injury. Nerve crush induces a similar SPRR1A expression level at 7 d, but levels decrease to baseline by 1 month (bottom). The number of days between nerve transection and animal death is shown at the top. Concentrations of SPRR1A protein in the DRG homogenates are reported at the bottom of each lane in nanograms of SPRR1A per microgram of total protein.

If SPRR1A induction after axotomy was correlated with the initial injury phase, this would suggest an immediate early gene function, whereas a correlation with the axonal regeneration phase might suggest a direct contribution to axon growth. To explore the temporal relationship between SPRR1A expression and sciatic nerve regeneration, DRGs were analyzed for SPRR1A protein at various times after resection of a piece of sciatic nerve. SPRR1A protein is not detectable 1 d after injury but is dramatically upregulated by 4 d and reaches peak levels 1-2 weeks after sciatic nerve injury (FIG. 1C). At maximal levels, SPRR1A constitutes 0.5% of total DRG protein or 6 ng of SPRR1A per microgram of total protein based on quantitative immunoblots using purified SPRR1A as a standard. Because the detection limit in this assay is 0.1 ng of SPRR1A per microgram of total protein, the increase in SPRR1A is >60-fold. SPRR1A levels are significantly reduced 1 month after injury. The decrease in SPRR1A at later times may reflect some reinnervation of appropriate and inappropriate targets with consequent downregulation of RAGs. To explore this further, another group of mice were subjected to sciatic nerve crush, which results in a similar degree of axonal damage but allows for more rapid and successful regeneration with complete functional recovery within 1 month. After midthigh sciatic nerve crush injury, DRG levels of SPRR1A protein follow a similar strong induction, but the downregulation is nearly complete at 1 month. This time course correlates well with hindlimb functional recovery after such injuries. Thus, DRG SPRR1A expression is bidirectionally regulated by axonal injury and target innervation.

Figure 2A:
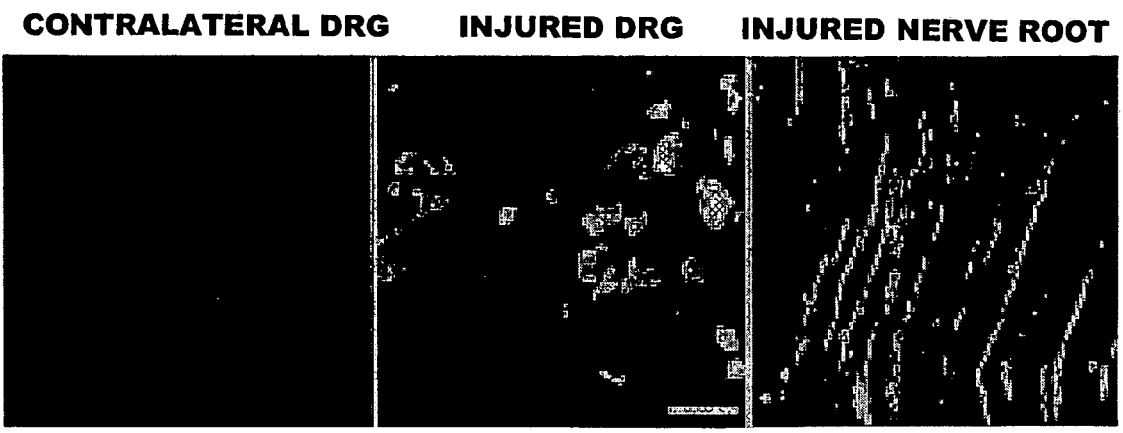
FIG. 2A is a series of images showing that SPRR1A immunofluorescence protein in the cell bodies and axons of DRG neurons 1 week after peripheral axotomy (injured). No SPRR1A immunoreactivity can be found in adult control DRGs (contralateral). Scale bar, 50 μm.
Figure 2B:
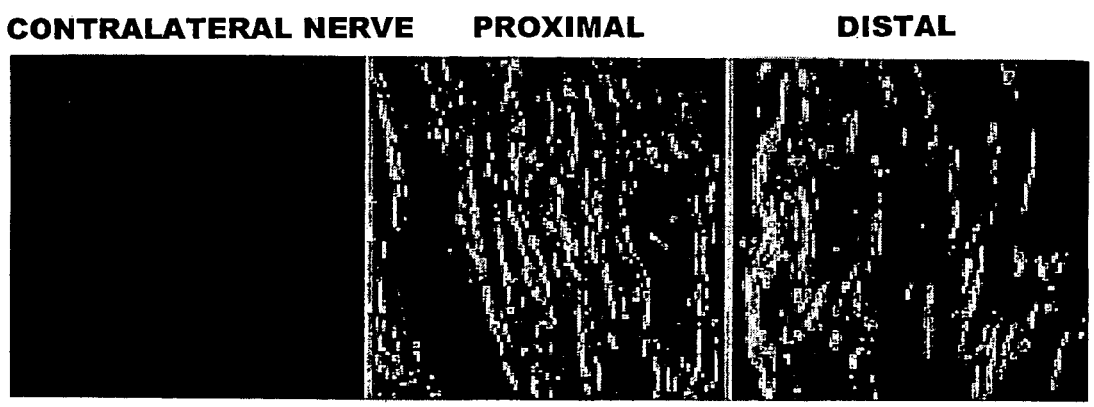
FIG. 2B is a series of images showing that SPRR1A protein is distributed throughout DRG regenerating axons, as revealed by SPRR1A immunoreactivity of sciatic nerve 1 week after a crush injury. SPRR1A-positive axons were found up to 20 mm distal from the crush site. The protein is absent in the contralateral (uninjured) nerve. Scale bar, 100 μm (from A).
Figure 2C:
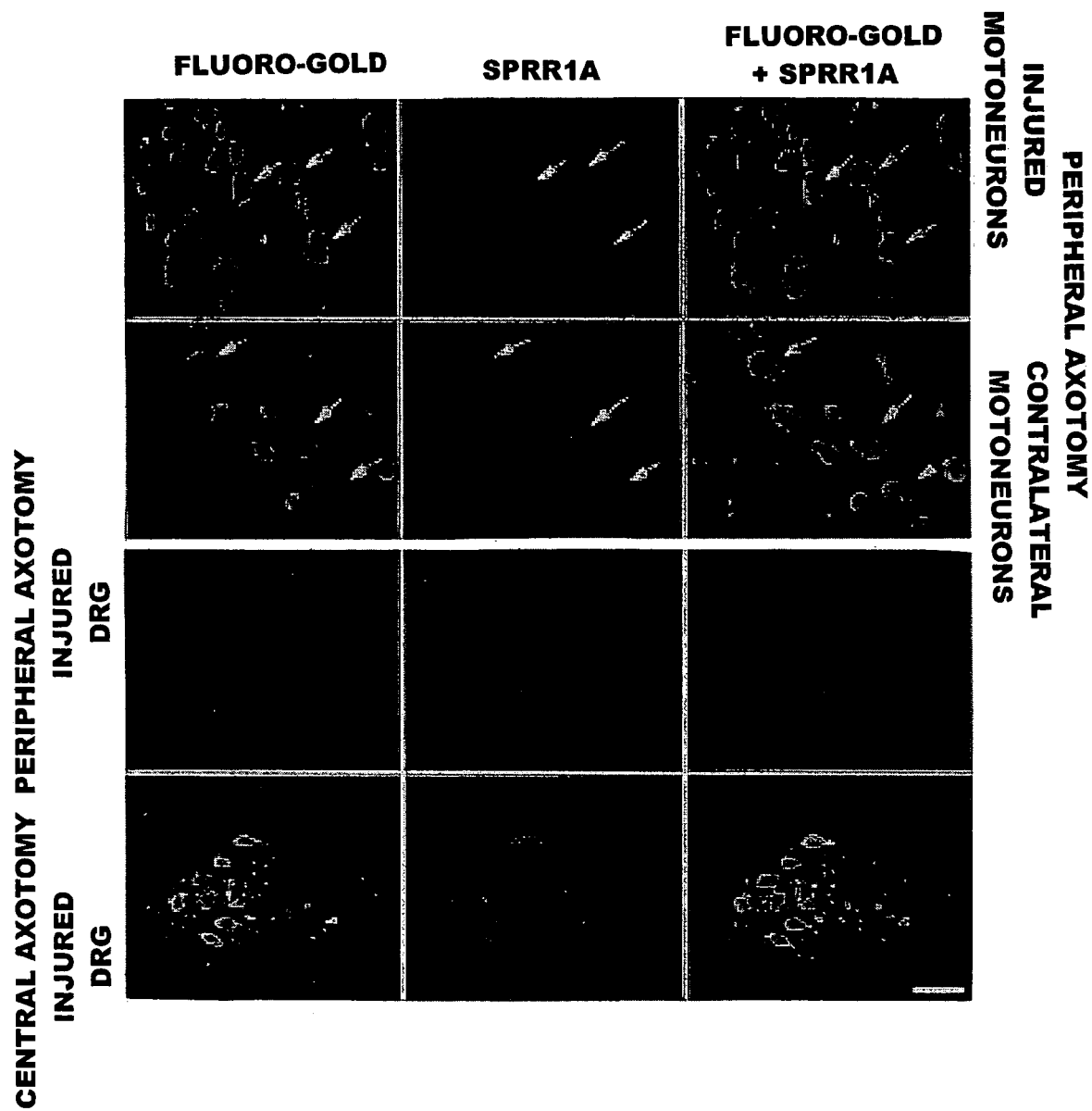
FIG. 2C is a collection of images showing that intense SPRR1A protein immunoreactivity co-localizes with Fluoro-Gold retrogradely labeled sensory and motor neurons ipsilateral to a sciatic nerve transection (peripheral axotomy, arrows). SPRR1A is slightly elevated in sensory neurons 1 week after thoracic SCI (central axotomy). SPRR1A is absent from the ventral horn contralateral to a sciatic nerve transection. Scale bar: first and second rows, 50 μm; third and fourth rows, 100 μm.

The DRG contains not only neurons but also fibroblasts, satellite cells, and Schwann cells. To assess the cellular origin of SPRR1A protein in axotomized DRGs, immunohistochemical experiments were conducted. The pattern of SPRR1A staining in DRGs is consistent with neuronal cell bodies and axonal processes (FIG. 2A). A nerve crush injury was performed to determine whether regenerating axons crossing the site of injury contained SPRR1A protein. Axons in sections both proximal and distal to the crush site showed intense SPRR1A immunoreactivity, demonstrating that the protein is transported throughout the regenerating axonal process (FIG. 2B). That the stained cells are regenerating DRG neurons is clear in samples retrogradely labeled with Fluoro-Gold from the injured sciatic nerve (FIG. 2C). By two criteria, SPRR1A appears to be expressed in most, if not all, subclasses of DRG neurons. First, the vast majority of Fluoro-Gold-positive neurons, 85±3%, also exhibited SPRR1A immunoreactivity. Second, the average cell diameter of Fluoro-Goldpositive and SPRR1A-positive neurons was indistinguishable (35±2 μm vs. 38±2 μm). Because different subsets of DRG neurons have distinct cell sizes, the observed size supports the hypothesis that SPRR1A is expressed by most axotomized DRG neurons.

SPRR1A protein localization in DRGs after spinal cord injury was examined by retrogradely labeling neuronal cell bodies with Fluoro-Gold injected at the site of injury. Low levels of SPRR1A protein were detected in DRG neurons after central axotomy (FIG. 2C), consistent with the immunoblots showing a slight increase in SPRR1A levels (FIG. 2C). The histologic studies also demonstrate that on a cell-by-cell basis, peripheral axotomy is a much stronger SPRR1A-inducing signal than is central injury.

The sciatic nerve transection injures axons from both DRG sensory neurons and spinal motoneurons. Examination of spinal cord sections reveals that retrogradely labeled axotomized motoneurons in the ventral horn exhibit SPRR1A expression to a similar extent as do DRG neurons (FIG. 2C). The contralateral ventral horn does not exhibit SPRR1A immunoreactivity. Thus, neurons situated in both the CNS and PNS strongly upregulate SPRR1A after peripheral axotomy.

S100C and p21/WAF expression are increased after sciatic nerve axotomy. The results from the microarray screen reveal a more than threefold upregulation of S100C (Table 1). S100C forms dimers and is a member of a family of small S100 proteins that exhibit EF-handtype $Ca^{2+}$-binding properties. Like SPRR1A, S100C is thought to be a structural component of the CE of epithelial cells (Robinson et al., 1997). It has also been implicated in the regulation of cytoskeletal functions via $Ca^{2+}$-dependent interaction with annexin I and F-actin (Naka et al., 1994; Mailliard et al., 1996; Sakaguchi et al., 2000). Other functions attributed to the S100 family include cell-cycle regulation, cell differentiation, cell growth, and metabolic control (Allen et al., 1996; Marti et al., 1996; Scotto et al., 1998).

p21/WAF1 is the third transcript induced after sciatic nerve axotomy whose expression is characterized in this study (FIG. 1B). p21, also known as WAF1, cyclin-dependent kinase-interacting protein 1, and senescent cell-derived inhibitor 1, is involved in cell-cycle regulation, cell differentiation, and tumor suppression (for review, see Cox, 1997; Gartel and Tyner, 1999). The p21 protein is a cyclin kinase inhibitor that inhibits G1 cyclin/cyclin-dependent kinase complexes (Harper et al., 1993; Xiong et al., 1993) and is activated by p53 (El-Deiry et al., 1993). In addition, like SPRR1A and S100C, p21 is induced by UV irradiation (Gorospe et al., 1998) and by phorbol esters (Zeng et al., 1997) in epithelial cells.

Figure 3A:
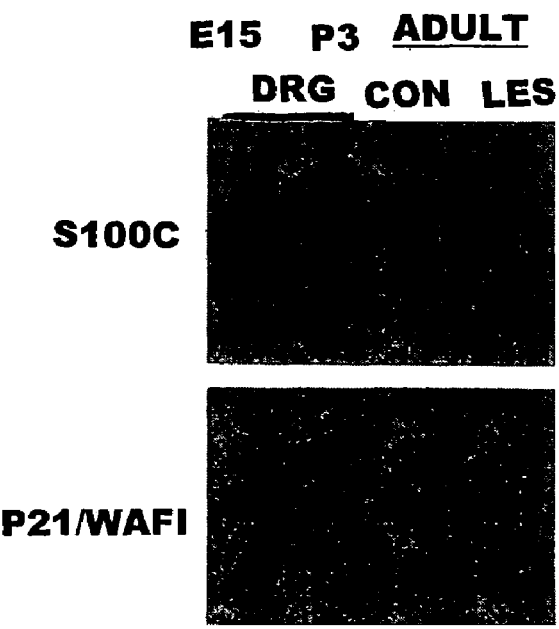
FIG. 3A is a pair of northern blots, showing analysis of s100c mRNA levels in lumbar DRGs from animals of different ages. Adult DRG samples were analyzed contralateral (CON) or ipsilateral (LES) to a sciatic nerve transection 1 week before death. A clear upregulation of the transcript after axotomy is evident. p21/waf1 mRNA levels are regulated in a similar manner in the lower panel. Two micrograms of total RNA were loaded in each lane.
Figure 3B:
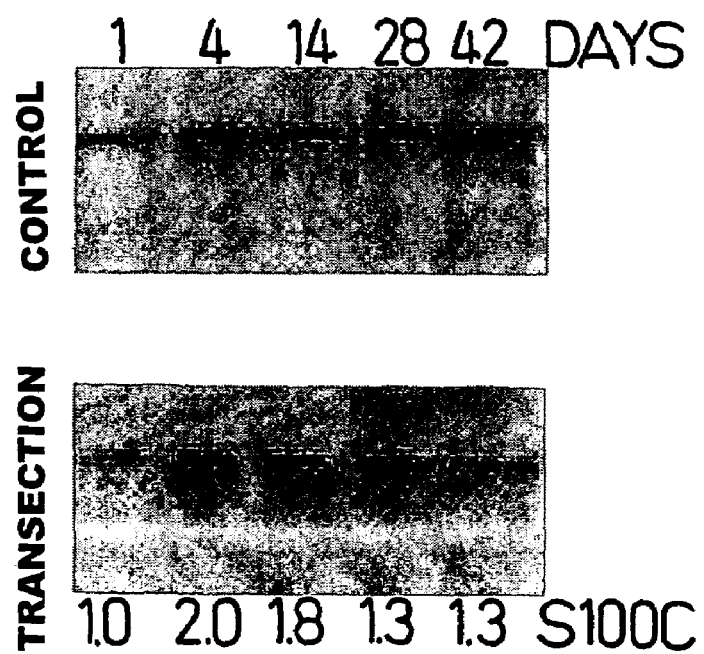
FIG. 3B is a pair of S100C immunoblots that demonstrate protein levels contralateral (CONTROL) or ipsilateral (TRANSECTION) to a sciatic nerve transection at the indicated times after lesion. Quantification of the relative levels of S100C protein in the axotomized DRG samples is reported at the bottom.
Figure 3C:
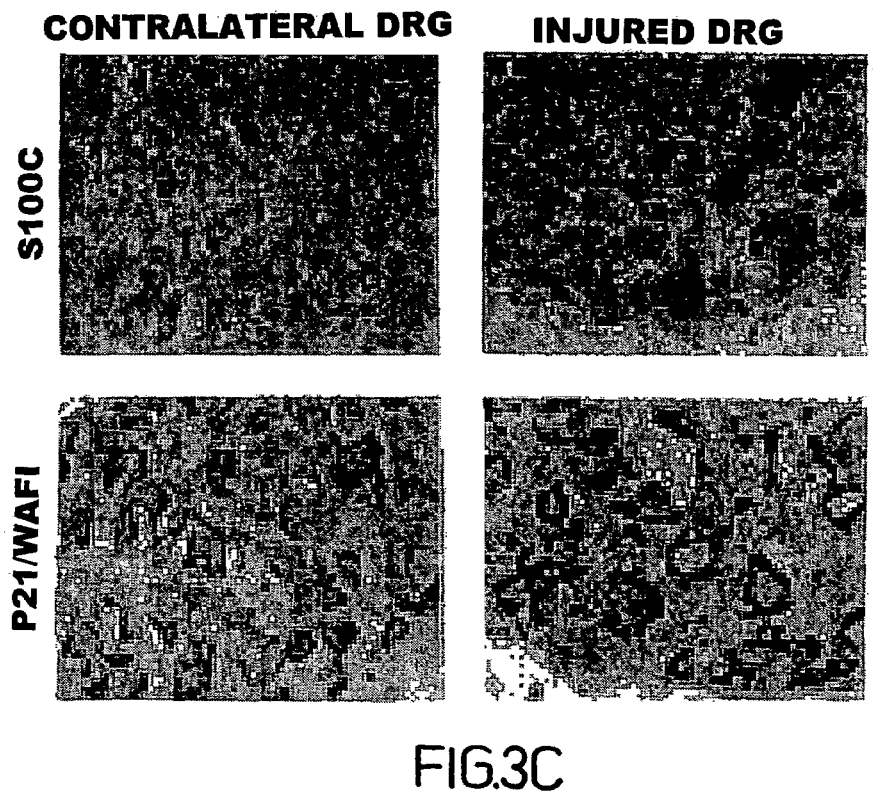
FIG. 3C is a collection of images in which In situ hybridization demonstrates s100c and p21/waf1 mRNA expression in lumbar DRGs contralateral or ipsilateral (injured) to sciatic nerve transection 1 week before death.
Figure 3D:
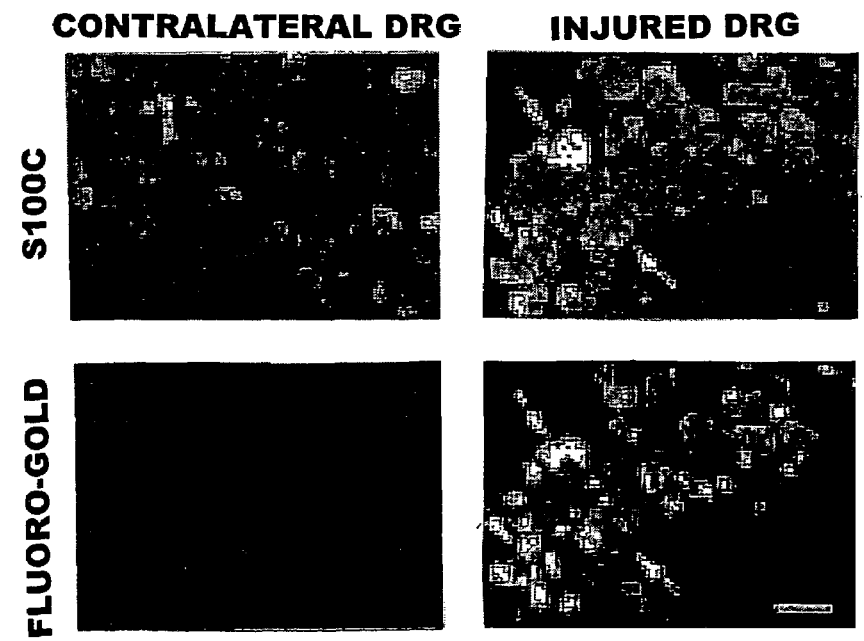
FIG. 3D is a collection of images illustrating that S100C immunostaining of DRG sections that were retrogradely labeled with Fluoro-Gold demonstrates that the protein is induced selectively in neurons that underwent transection 1 week earlier at the midthigh (arrows). Scale bar, 50 μm.

Northern blot analysis confirms the upregulation of s100c and p21/waf1 after peripheral axotomy. s100c and p21/waf1 are also expressed in DRGs at embryonic and early postnatal stages, contrary to sprr1a but similar to gap-43 (FIG. 3A). At the protein level, S100C is elevated 4 d after axotomy, remains increased up to 2 weeks after injury, and returns to normal levels by 1 month (FIG. 3B), a time course similar to that of SPRR1A and GAP-43. In the DRG homogenates composed of both neuronal and nonneuronal elements, the S100C protein level is induced by 100%. The cellular identity of the cells overexpressing S100C after axotomy was investigated by in situ hybridization and immunocytological experiments. Both s100c and p21 mRNA are localized to neuronal cell bodies in the DRG by in situ hybridization experiments (FIG. 3C). Fluoro-Gold retrograde labeling of injured DRG neurons demonstrates that regenerating DRG neurons exhibit increased S100C expression (FIG. 3D). Because these neurons compose approximately one-half of the DRG cell population, the results of FIGS. 3A,C suggest that S100C protein levels are approximately threefold higher in axotomized neurons.

SPRR1A and S100C are localized to F-actin structures. In the CE, SPRR1A and S100C, along with other proteins, are covalently cross-linked by transglutaminases (TGases) to generate a rigid structure that alters cellular properties (Greenberg et al., 1991; Hohl et al., 1995). To consider whether SPRR1A and S100C might have a related function in neurons, SPRR1A cross-linking and TGase activity were assayed. Immunoblot experiments of protein from control and lesion DRGs revealed only monomeric SPRR1A (FIG. 1B) and no insoluble aggregated SPRR1A immunoreactivity. Furthermore, no consistent or significant difference in DRG TGase activity between control and sciatic nerve lesion samples could be detected. These findings demonstrate that SPRR1A and S100C do not participate in a CE-like structure in injured DRGs.

Figure 4A:
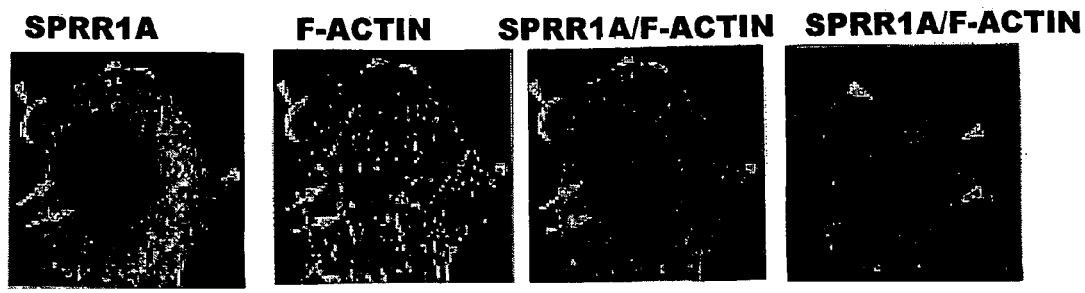
FIG. 4A is a series of images of COS-7 cells transfected with pCDNA3.1-SPRR1A-Myc. SPRR1A immunoreactivity co-localizes with F-actin-rich structures, predominantly at dorsal and leading edge ruffles (arrowheads). SPRR1A is absent from actin-rich stress fibers (arrows). The left three panels show double labeling of one cell, and the extreme right panels show a different cell.
Figure 4B:
FIG. 4B is a series of images of COS-7 cells transfected with pCDNA3.1-S100C-Myc-His. S100C immunoreactivity colocalizes with F-actin (ruffles, arrowheads). The left three panels show double labeling of one cell, and the extreme right panel shows a different cell.
Figure 4C:
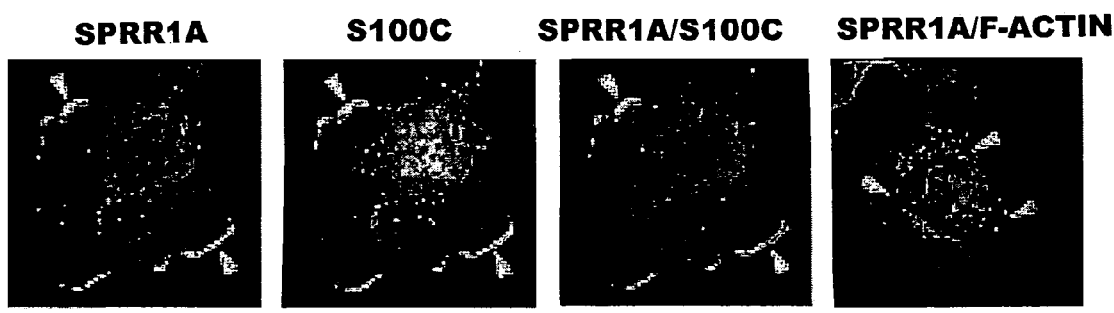
FIG. 4C is a series of images of COS-7 cells cotransfected with pCDNA3.1-SPRR1A-Myc and pDNA3.1-S100C-Myc-His. SPRR1A and S100C immunoreactivity codistributed at leading edge and dorsal ruffles (arrowheads). S100C was detected by staining with monoclonal anti-His antibodies. The left three panels show double labeling of one cell, and the extreme right panel shows a different cell.
Figure 4D:
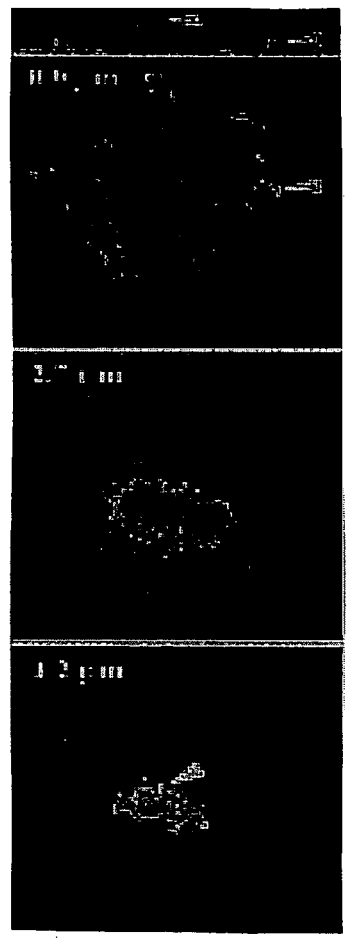
FIG. 4D is a collection of images showing the distribution of SPRR1A and F-actin in a pDNA3.1-SPRR1A-Myc-transfected COS-7 cell examined in three dimensions. Top, Vertical (z-axis) cross section at the level of the blue arrows for the lower three panels. The numbers on the lower three panels refer to the distance above the substrate. Note the predominant distribution of SPRR1A to dorsal and leading edge ruffles (arrowheads). A dorsal ruffle is shown to protrude into the upper region of the cell.

To consider alternative mechanisms of SPRR1A function, subcellular distribution of the protein was examined, considering what is known about S100C S100C binds to F-actin in the presence of $Ca^{2+}$ and alters cytoskeletal function in nonneuronal cells (Sakaguchi et al., 2000). Because F-actin dynamics play a major role in regulating axonal growth cone motility, it was believed that axotomy-induced SPRR1A and S100C protein might modulate F-actin structures in concert. Transient expression of SPRR1A and S100C in non-neuronal cells allowed for a careful examination of their localization relative to F-actin. Both SPRR1A and S100C are highly concentrated in certain F-actin-rich structures (FIGS. 4A-C). SPRR1A immunoreactivity in COS-7 cells is enriched in serpentine structures consistent with dorsal ruffles and in leading edge ruffles. A reconstruction of a z-axis series from confocal microscopy verified the localization of SPRR1A to dorsal ruffles (FIG. 4D). SPRR1A protein is not localized to F-actin-positive stress fibers. The previous description of S100C affinity for F-actin is evident in our studies (FIG. 4B). Similar to SPRR1A, S100C protein is present in dorsal and leading edge ruffles. Contrary to the exclusive localization of SPRR1A in these structures, S100C also localizes to stress fibers. The presence of both SPRR1A and S100C in membrane ruffles suggests that they contribute to similar or identical subcellular structures. A direct examination of doubly transfected cells confirms that the two proteins codistribute in dorsal and leading edge ruffles. Variation in F-actin structures from cell to cell is great in these cultures, and no pronounced shift in the type or total number of F-actin-rich structures in SPRR1A-expressing cells was observed.

Figure 4E:
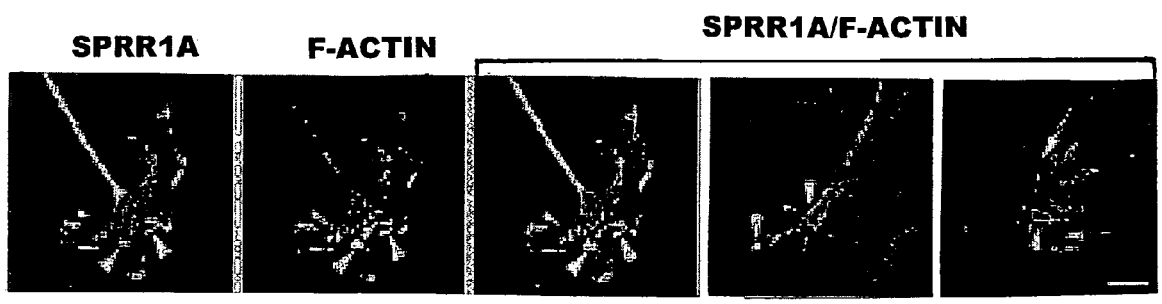
FIG. 4E is a series of images showing chick E7 DRG cultures infected with HSV-SPRR1A and examined for SPRR1A and F-actin distribution 24 hr later by confocal microscopy. In axonal growth cones (left three panels show one growth cone, and the next panel shows a second growth cone) and fibroblasts (right panel), note the similar distribution of SPRR1A and F-actin in linear aggregates and ruffles (arrowheads). Other F-actin-rich structures (arrows), such as stress fibers, are not enriched in SPRR1A. Scale bar, 50 µm.

SPRR1A was then examined for localization to F-actin-rich regions of axonal growth cones. A recombinant HSV preparation was used to express SPRR1A in chick embryonic DRG cultures. The infected fibroblasts in these cultures exhibit an SPRR1A distribution that is essentially identical to the transfected COS-7 cells (FIG. 4B). Infected neurons exhibit SPRR1A immunoreactivity throughout their axons (FIG. 4E), similar to the axonal localization seen in tissue samples from sciatic nerve transected animals (FIG. 2). Higher magnification of well-spread axonal growth cones in these cultures reveals SPRR1A immunoreactivity colocalized with F-actin in discrete linear ridges and aggregates in axonal growth cones. The pattern is consistent with dorsal and leading edge ruffles.

Whereas SPRR1A is colocalized with F-actin in ruffles, other F-actin-rich structures, such as stress fibers and filopodia, do not exhibit specific concentrations of SPRR1A. This suggests that SPRR1A does not bind directly to F-actin but rather to actin-associated protein(s) enriched in ruffles. To verify whether or not F4 SPRR1A is able to bind F-actin directly, actin cosedimentation and immunoprecipitation assays were performed. These methods reveal no direct physical association of SPRR1A with F-actin in the presence or absence of S100C protein. Thus, unidentified proteins specific to membrane ruffles must account for the colocalization of F-actin and SPRR1A.

Figure 5A:
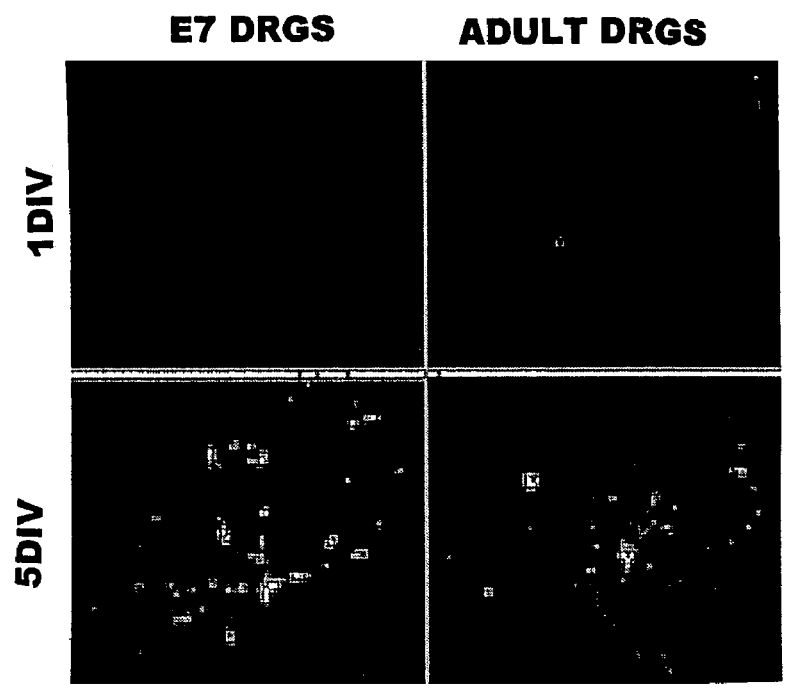
FIG. 5A is a collection of images illustrating that SPRR1A promotes axonal outgrowth in embryonic neurons. Endogenous SPRR1A protein immunoreactivity is not detected in chick E7 and adult mouse DRGs cultured for 1 DIV but is present after 5 DIV by immunofluorescence. Scale bar, 100 µm.
Figure 5B:
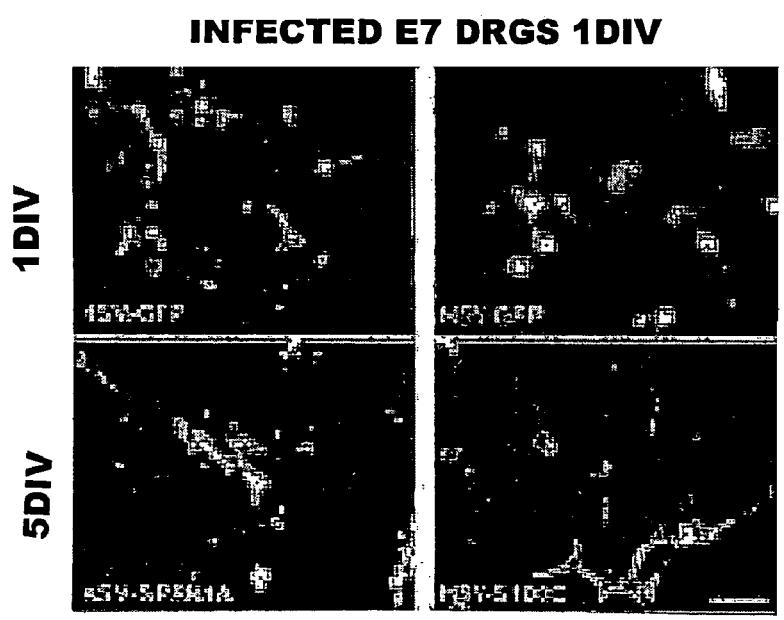
FIG. 5B is a collection of images showing that overexpression of SPRR1A and S100C protein in chick E7 DRGs via recombinant HSV infection increases axonal growth compared with HSV-EGFP-infected cells. EGFP-, SPRR1A-, and S100C-expressing neurons are identified by EGFP fluorescence, SPRR1A immunoreactivity, and S100C immunoreactivity, respectively.
Figure 5C:
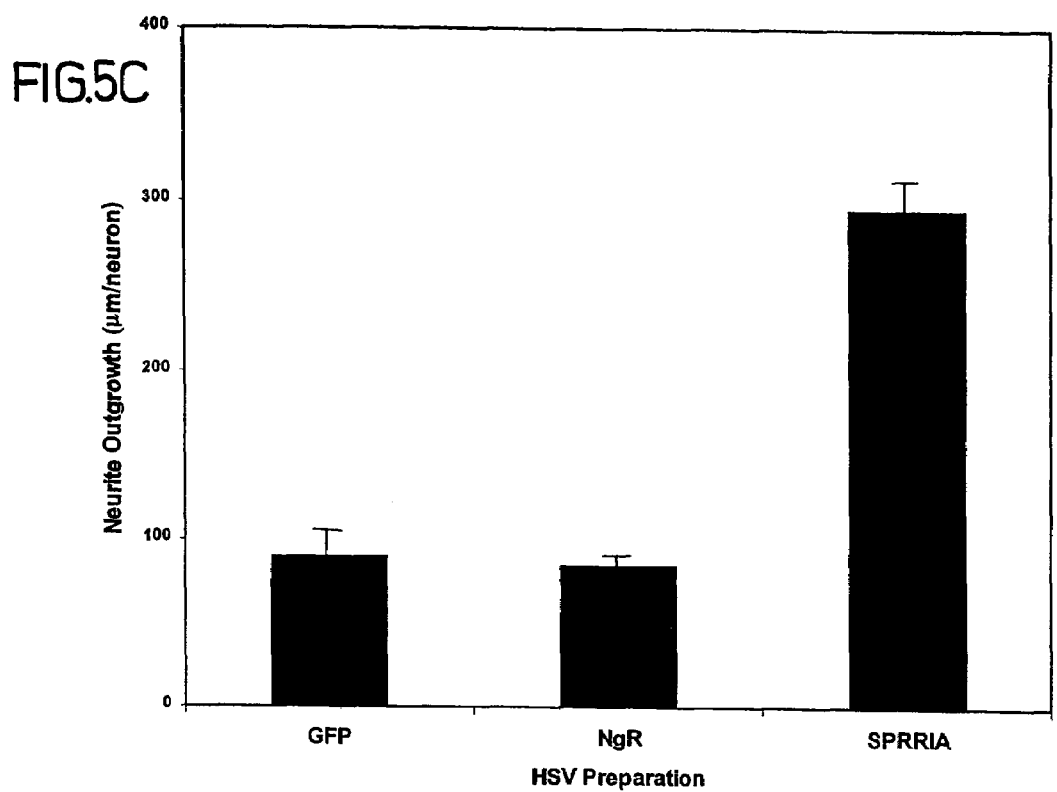
FIG. 5C is a graph depicting neurite outgrowth in neurons expressing EGFP, Nogo-66 receptor (NgR, as a control), or SPRR1A via recombinant HSV infection. A significant ($p \leq 0.05$, Student's two-tailed t test) increase in outgrowth is observed in HSVSPRR1A-infected cultures 24 hr after plating. Data are means ±SEM from five experiments.
Figure 5D:
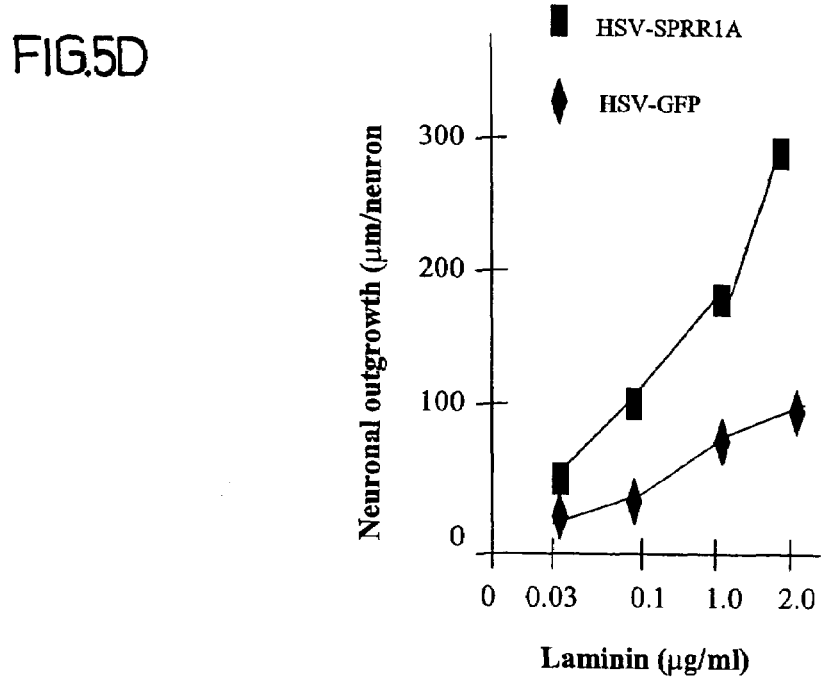
FIG. 5D is a graph depicting DRG neurons infected with HSV-EGFP or HSV-SPRR1A cultured on the indicated concentrations of laminin. Mean neurite outgrowth per infected neuron is reported (±SEM).

SPRR1A and S100C increase axonal outgrowth in embryonic neurons. The data indicate that expression of SPRR1A and S100C is correlated with axonal regeneration and that the proteins are colocalized with F-actin. Do SPRR1A and S100C promote axonal regeneration? A functional contribution to axonal regeneration was examined in cultured DRG neurons. Embryonic chick DRG or adult mouse DRG neurons do not express SPRR1A immediately after plating, but high levels develop by 5 d in vitro (DIV) (FIG. 5A). Induction is much more robust in adult neurons. As seen in tissue sections, the protein is present in axons in which it might directly alter outgrowth. Because E7 chick DRGs do not express the endogenous protein within the first 24 hours in vitro, effects of SPRR1A introduction into these cells were examined. Infection with an HSV preparation directing SPRR1A expression results in a threefold increase in outgrowth for infected SPRR1A immunoreactive cells at 1 DIV (FIGS. 5B,C). This appears to alter the intrinsic growth properties of the neurons, and the SPRR1A enhancement of growth is observed over a range of laminin substrate concentrations (FIG. 5D). As an alternative method for increasing SPRR1A levels, recombinant SPRR1A protein was triturated into DRG neurons (FIG. 5E). A similar increase in neurite outgrowth is observed. S100C is normally expressed in embryonic neurons. In recombinant HSV-S100C experiments, overexpression of S100C results in a moderate 60% increase in neurite outgrowth (FIGS. 5B,F). Thus, neuronal SPRR1A, and to a lesser extent S100C, can directly promote axonal outgrowth.

Figure 6A:
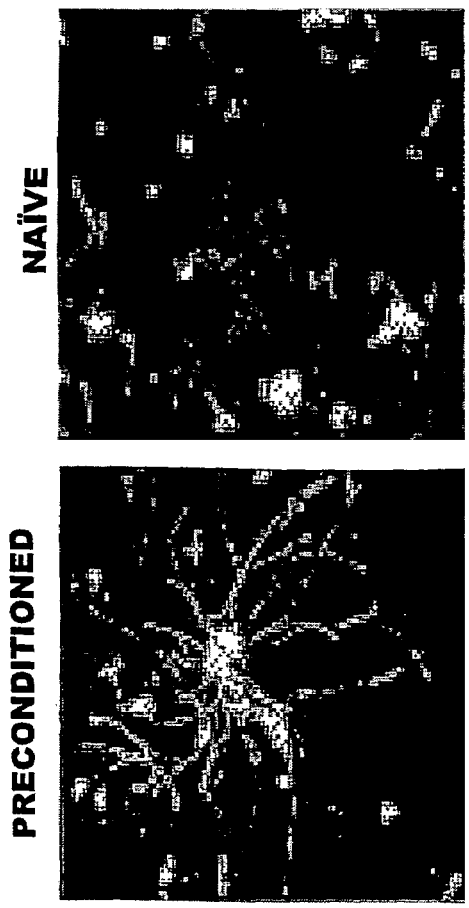
FIG. 6A is a pair of images illustrating that SPRR1A promotes axonal outgrowth in adult neurons and on inhibitory substrates. Phalloidin staining of adult mouse DRGs after 1 DIV illustrates the different modes of growth that characterize naive and preconditioned neurons. Preconditioned DRGs were removed and plated 4 d after sciatic nerve axotomy. Whereas naive DRGs extend short and highly branched neurites, preconditioned DRGs grow neurites that are elongated and sparsely branched.
Figure 6B:
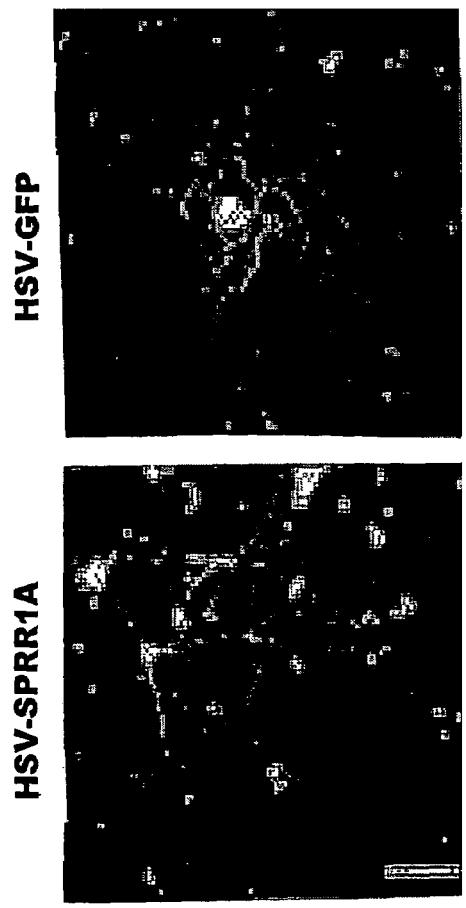
FIG. 6B is a images illustrating that overexpression of SPRR1A protein in adult mouse DRGs via recombinant HSV infection increases axonal growth and decreases branching compared with HSV-EGFP-infected cells. EGFP- and SPRR1A-expressing neurons are identified by EGFP fluorescence and SPRR1A immunoreactivity, respectively. Scale bar, 100 µm.

SPRR1A increases axonal outgrowth in adult neurons. Although the embryonic neuron experiments demonstrate that SPRR1A can promote axonal growth, studies of adult neurons are more relevant to nerve regeneration. Adult DRG neurons are known to display distinct modes of growth in culture, after peripheral nerve axotomy or removal of the ganglion, with a time-dependent transition from a branching to an elongating mode of outgrowth. Because endogenous SPRR1A is not expressed during the first 24 hr after plating adult mouse DRGs, SPRR1A expression altered outgrowth patterns from these neurons was investigated. SPRR1A-expressing neurons exhibit an 80% increase in outgrowth compared with GFP-expressing neurons (FIGS. 6A-C). The increase is similar in magnitude to that achieved by a preconditioning axotomy. Axonal branching was decreased 50% in SPRR1A-expressing neurons compared with GFP-expressing neurons (FIG. 6D). Again, this difference is nearly identical to the decreased branching observed for preconditioned neurons. Thus, acute SPRR1A expression in culture promotes the branching-to elongating morphological switch and fully mimics the effects of a preconditioning axotomy.

SPRR1A increases axonal outgrowth of embryonic neurons on inhibitory substrates. In vivo, regenerating neurons frequently encounter inhibitory substrates that limit their outgrowth. Among these inhibitors, CNS myelin containing Nogo may play a role in preventing adult mammalian CNS axon regeneration (GrandPre et al., 2000). Therefore, SPRR1A overexpression modulation of the sensitivity to these inhibitors was inhibited. Axonal sensitivity to inhibition by Nogo and CNS myelin is obvious in chick E13 DRG neuronal cultures. Overexpression of SPRR1A has a stimulatory effect on outgrowth over Nogo-66 and CNS myelin but does not overcome the inhibition (FIGS. 6E,F). The fractional increase in outgrowth induced by SPRR1A is similar for neurons on laminin, CNS myelin, and Nogo. Thus, SPRR1A expression alters the basal propensity for axonal growth but not the responsiveness to these nonpermissive substrates. Depletion or blockade of SPRR1A protein decreases outgrowth in adult neurons If SPRR1A expression plays a significant role in the regenerative outgrowth of adult neurons, then reduction in SPRR1A activity should reduce axon regeneration. To assess whether SPRR1A is necessary for axonal regeneration, adult DRG neurons were harvested 4 d after a sciatic nerve transection (preconditioned neurons), and SPRR1A was suppressed by one of two methods. In one protocol, adult DRG neurons were removed and plated for 36 hr in the presence of sense, antisense, or no oligonucleotide. Western blotting and immunohistochemistry verified that SPRR1A expression was significantly and selectively decreased after treatment with antisense oligonucleotides complimentary to the translation initiation site of the sprr1a sequence (FIGS. 7A-C). Depletion of SPRR1A protein in adult preconditioned neurons with antisense oligonucleotides results in a significant decrease in neurite length (FIGS. 7C,D). Antisense-treated preconditioned neurons display outgrowth capabilities that resemble those of naive neurons. Not only is axon outgrowth reduced, but axonal branching indices also show a marked increase in the antisense-treated cultures (FIG. 7E). The lack of effect of these antisense oligonucleotides on the naive neurons that do not express SPRR1A further confirms the selectivity of action.

Figure 7F:
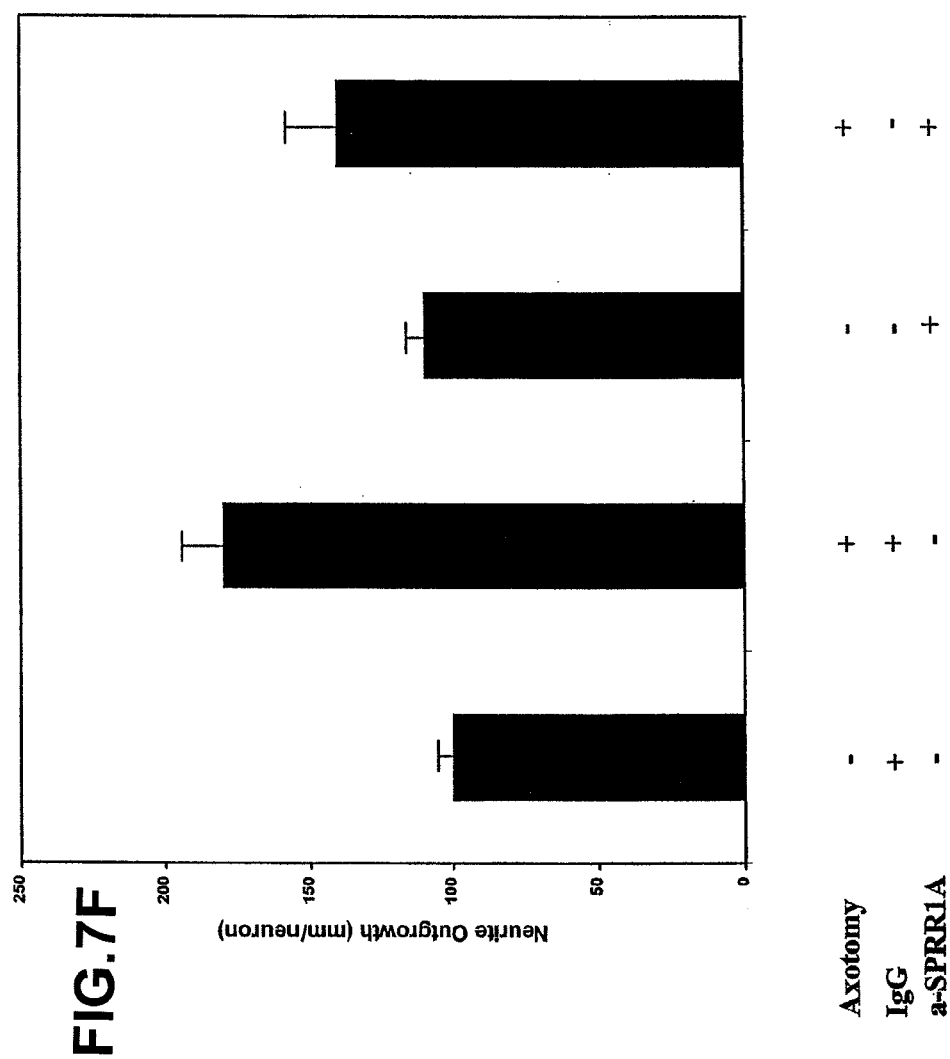
FIG. 7F is a collection of images showing neurite outgrowth in preconditioned adult neuronal cultures triturated in the presence of rabbit IgG or α-SPRR1A. Axonal length was decreased after antibody-mediated blockade of SPRR1A protein compared with rabbit IgG. Scale bar, 100 μm. G, Axonal growth was measured in naive and preconditioned neurons triturated with control antibody, rabbit IgG (0.2 mg/ml), or affinity-purified SPRR1A antibody (0.2 mg/ml). Neurite length was decreased in α-SPRR1A-triturated preconditioned neurons relative to IgG-treated preconditioned neurons (p≦0.05, Student's two-tailed t test). No change in neurite outgrowth was observed in naive neurons triturated with α-SPRR1A. Data are means ±SEM from three experiments.

SPRR1A function was also reduced by trituration of naive and preconditioned adult DRG neurons with affinity-purified SPRR1A antibody. Similar to the antisense oligonucleotide treatment, anti-SPRR1A antibody treatment decreased neurite outgrowth in the adult preconditioned neurons (FIGS. 7F). This inhibition was selective in that rabbit IgG had no effect and anti-SPRR1A-treated naive neurons (lacking SPRR1A) did not exhibit altered outgrowth. Thus, two methods confirm that SPRR1A contributes to the axotomy-induced morphological switch from a branching to an elongating mode of growth.

Figure 8:
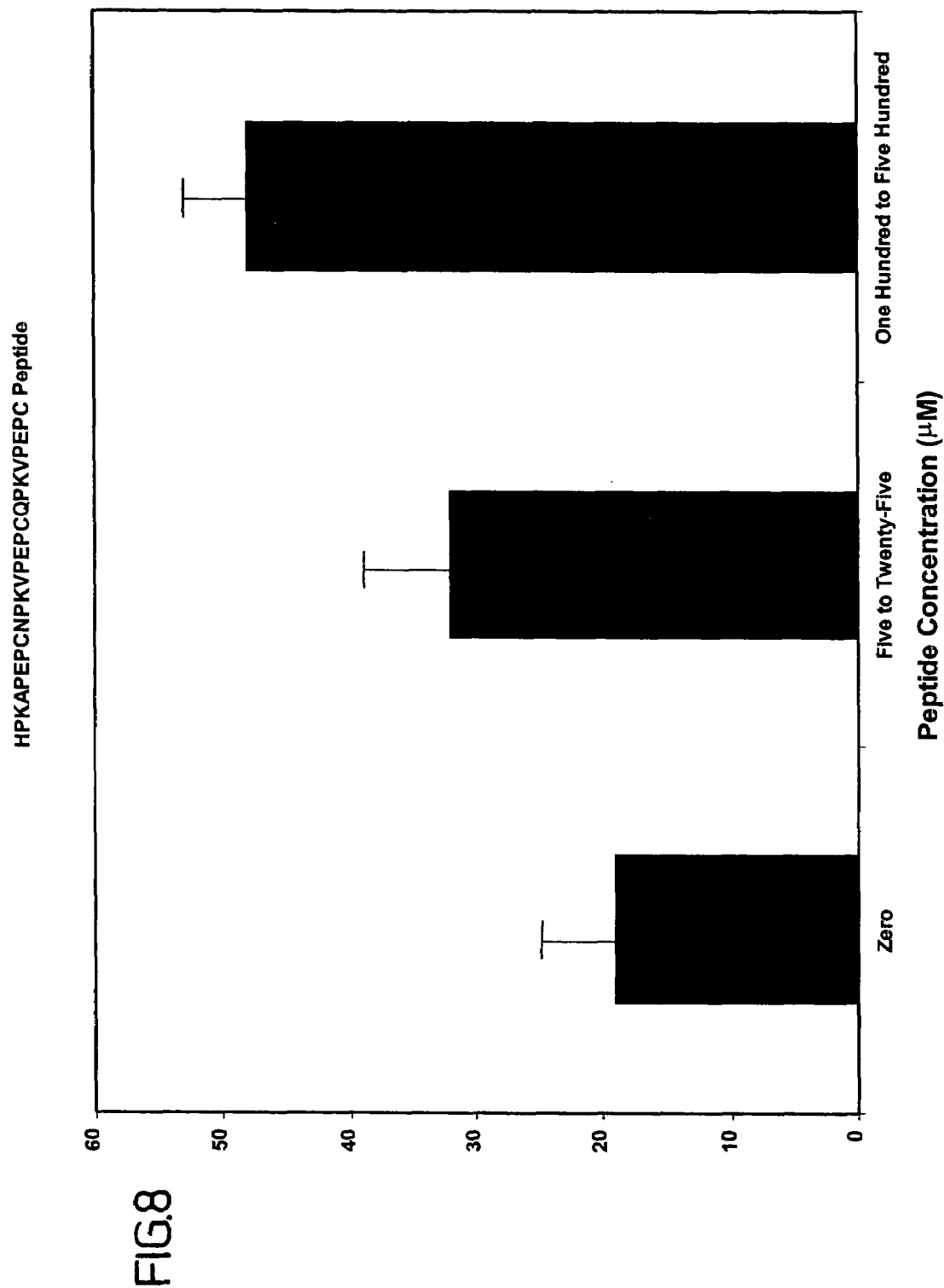
FIG. 8 is a graph that shows the SPRR1A-derivative peptide concentration-dependent stimulation of axonal outgrowth. The synthetic 24 amino acid peptide acetyl-HP-KAPEPCNPKVPEPCQPKVPEPC-amide (SEQ ID NO:3) was introduced into E8 chick DRGs by trituration. Neurite outgrowth was assessed 6 hours after plating on a laminin substrate.

An SPRR1A-derived peptide acts as an agent to promote axon regeneration. As described above, SPRR1A protein levels increase after sciatic nerve transection in DRG neurons. Furthermore the functional experiments, in which the protein is introduced into neurons by protein trituration or viral infection, demonstrate that this protein is capable of augmenting neurite outgrowth. SPRR1A is a relatively small protein consisting of 145 amino acids that can be divided into three regions, the carboxyl terminus, the amino terminus and a central domain formed by proline rich repeats. Since most of the SPRR1A protein consists of the repeating XPKXPEPC (SEQ ID NO:6) octapeptide sequence (>70%) at its core, the dependence of the in vitro growth-promoting role of SPRR1A on these repeats was investigated. To this end, a 24 amino acid peptide consisting of three repeats was synthesized. SEQ ID NO:3, HPKAPEPCNPKVPEPCQP-KVPEPC, was used with the amino terminus acetylated and the carboxyl terminus amidated. This 24 amino acid peptide was triturated into E8 chick DRGs and neurite length was measured 6 hours after the cells were plated on laminin (FIG. 8). Average neurite outgrowth is enhanced 1.7-fold when cells are treated with 5-25 µM peptide and neurite outgrowth is enhanced 2.5-fold when the cells are treated with 100-500 µM peptide. These results indicate that the octapeptide repeats in SPRR1A sequence are the domains responsible for altering neurite extension. Furthermore, the data indicate that a smaller peptide derivative with potential for in vivo administration has full SPRR1A efficacy in promoting outgrowth.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

REFERENCES

Allen B G, Durussel I, Walsh M P, Cox J A (1996) Characterization of the Ca$^{2+}$-binding properties of calgizzarin (S100C) isolated from chicken gizzard smooth muscle. Biochem Cell Biol 74:687-694.

Bomze H M, Bulsara K R, Iskandar B J, Caroni P, Skene J H (2001) Spinal axon regeneration evoked by replacing two growth cone proteins in adult neurons. Nat Neurosci 4:38-43.

Chong M S, Woolf C J, Haque N S, Anderson P N (1999) Axonal regeneration from injured dorsal roots into the spinal cord of adult rats. J Comp Neurol 410:42-54.

Cox L S (1997) Multiple pathways control cell growth and transformation: overlapping and independent activities of p53 and p21Cip1/WAF1/Sdi1. J Pathol 183:134-140.

Dickson B J (2001) Rho GTPases in growth cone guidance. Curr Opin Neurobiol 11: 103-110.

Duggan D J, Bittner M, Chen Y, Meltzer P, Trent J M (1999) Expression profiling using cDNA microarrays. Nat Genet 21:10-14.

Elde R, Cao Y H, Cintra A, Brelje T C, Pelto-Huikko M, Junttila T, Fuxe K, Pettersson R F, Hokfelt T (1991) Prominent expression of acidic fibroblast growth factor in motor and sensory neurons. Neuron 7:349-364.

El-Deiry W S, Tokino T, Velculescu V E, Levy D B, Parsons R, Trent J M, Lin D, Mercer W E, Kinzler K W, Vogelstein B (1993) WAF1, a potential mediator of p53 tumor suppression. Cell 75:817-825.

Ernfors P, Henschen A, Olson L, Persson H (1989) Expression of nerve growth factor receptor mRNA is developmentally regulated and increased after axotomy in rat spinal cord motoneurons. Neuron 2:1605-1613.

Fawcett J W, Asher R A (1999) The glial scar and central nervous system repair. Brain Res Bull 49:377-391.

Fournier A E, Strittmatter S M (2001) Repulsive factors and axon regeneration in the CNS. Curr Opin Neurobiol 11:89-94.

Fournier A E, GrandPre T, Strittmatter S M (2001) Identification of a receptor mediating Nogo-66 inhibition of axonal regeneration. Nature 409:341-346.

Fu S Y, Gordon T (1997) The cellular and molecular basis of peripheral nerve regeneration. Mol Neurobiol 14:67-116.

Gartel A L, Tyner A L (1999) Transcriptional regulation of the p21(WAF1/CIP1) gene. Exp Cell Res 246:280-289.

Gibbs S, Fijneman R, Wiegant J, van Kessel A G, van De Putte P, Backendorf C (1993) Molecular characterization and evolution of the SPRR family of keratinocyte differentiation markers encoding small proline-rich proteins. Genomics 16:630-637.

Gillen C, Korfhage C, Muller H W (1997) Gene expression in nerve regeneration. The Neuroscientist 3:112-122.

Gispen W H, Nielander H B, De Graan P N, Oestreicher A B, Schrama L H, Schotman P (1991) Role of the growth-associated protein B-50/GAP-43 in neuronal plasticity. Mol Neurobiol 5:61-85.

Gonzalez M, Cambiazo V, Maccioni R B (1998) The interaction of Mip-90 with microtubules and actin filaments in human fibroblasts. Exp Cell Res 239:243-253.

Gordon T (1983) Dependence of peripheral nerves on their target organs. In: Somatic and autonomic nerve-muscle interactions (Burnstock G, Vrbova G, O'Brien R A, eds), pp 289-323. New York: Elsevier.

Gorospe M, Wang X, Holbrook N J (1998) p53-dependent elevation of p21 Waf1 expression by UV light is mediated through mRNA stabilization and involves a vanadate-sensitive regulatory system. Mol Cell Biol 18:1400-1407.

Goshima Y, Nakamura F, Strittmatter P, Strittmatter S M (1995) Collapsin-induced growth cone collapse mediated by an intracellular protein related to UNC-33. Nature 376:509-514.

Grafstein B, McQuarrie J G (1978) Role of the nerve cell body in axonal regeneration. In: Neuronal plasticity (Cotman C W, ed), pp 155-196. New York: Raven.

GrandPre T, Nakamura F, Vartanian T, Strittmatter S M (2000) Identi-fication of the Nogo inhibitor of axon regeneration as a reticulon protein. Nature 403:439-444.

Greenberg C, Birckbichler P, Rice R (1991) Transglutaminases: multifunctional cross-linking enzymes that stabilize tissues. FASEB J 5:3071-3077.

Harper J W, Adami G R, Wei N, Keyomarsi K, Elledge S J (1993) The p21 Cdk-interacting protein Cip1 is a potent inhibitor of G1 cyclindependent kinases. Cell 75:805-816.

Hohl D, de Viragh P A, Amiguet-Barras F, Gibbs S, Backendorf C, Huber M (1995) The small proline-rich proteins constitute a multigene family of differentially regulated cornified cell envelope precursor proteins. J Invest Dermatol 104:902-909.

Jin Z, Strittmatter S M (1997) Rac1 mediates collapsin-1-induced growth cone collapse. J Neurosci 17:6256-6263.

Kalil K, Skene J H (1986) Elevated synthesis of an axonally transported protein correlates with axon outgrowth in normal and injured pyramidal tracts. J Neurosci 6:2563-2570.

Kartasova T, van de Putte P (1988) Isolation, characterization, and Uv-stimulated expression of two families of genes encoding polypeptides of related structure in human epidermal keratinocytes. Mol Cell Biol 8:2195-2203.

Kartasova T, van Muijen G N, van Pelt-Heerschap H, van de Putte P (1988) Novel protein in human epidermal keratinocytes: regulation of expression during differentiation. Mol Cell Biol 8:2204-2210.

Katz F, Ellis L, Pfenninger K H (1985) Nerve growth cones isolated from fetal rat brain. III. Calcium-dependent protein phosphorylation. J Neurosci 5:1402-1411.

Kiryu S, Yao G L, Morita N, Kato H, Kiyama H (1995) Nerve injury enhances rat neuronal glutamate transporter expression: identification by differential display PCR. J Neurosci 15:7872-7878.

Kobayashi N R, Bedard A M, Hincke M T, Tetzlaff W (1996) Increased expression of BDNF and trkB mRNA in rat facial motoneurons after axotomy. Eur J Neurosci 8:1018-1029.

Krekoski C A, Parhad I M, Clark A W (1996) Attenuation and recovery of nerve growth factor receptor mRNA in dorsal root ganglion neurons following axotomy. Neurosci Res 43:1-11.

Liu R Y, Snider W D (2001) Different signaling pathways mediate regenerative versus developmental sensory axon growth. J Neurosci 21:RC164:1-5.

Luo Z D, Chaplan S R, Higuera E S, Sorkin L S, Stauderman K A, Williams M E, Yaksh T L (2001) Upregulation of dorsal root ganglion α2δ calcium channel subunit and its correlation with allodynia in spinal nerve-injured rats. J Neurosci 21:1868-1875.

Mailliard W S, Haigler H T, Schlaepfer DD (1996) Calcium-dependent binding of S100C to the N-terminal domain of annexin I. J Biol Chem 271:719-725.

Marchionni M A, Goodearl A D, Chen M S, Bermingham-McDonogh O, Kirk C, Hendricks M, Danehy F, Misumi D, Sudhalter J, Kobayashi K (1993) Glial growth factors are alternatively spliced erbB2 ligands expressed in the nervous system. Nature 362:312-318.

Marti T, Erttmann K D, Gallin M Y (1996) Host-parasite interaction in human onchocerciasis: identification and sequence analysis of a novel human calgranulin. Biochem Biophys Res Commun 221:454-458.

Moskowitz P F, Oblinger M M (1995) Sensory neurons selectively upregulate synthesis and transport of the βIII-tubulin protein during axonal regeneration. J Neurosci 15:1545-1555.

Muma N A, Hoffman P N, Slunt H H, Applegate M D, Lieberburg I, Price D L (1990) Alterations in levels of mRNAs coding for neurofilament protein subunits during regeneration. Exp Neurol 107:230-235.

Naka M, Qing Z X, Sasaki T, Kise H, Tawara I, Hamaguchi S, Tanaka T (1994) Purification and characterization of a novel calcium-binding protein, S100C, from porcine heart. Biochim Biophys Acta 1223:348-353.

Nakamura F, Tanaka M, Takahashi T, Kalb R G, Strittmatter S M (1998) Neuropilin-1 extracellular domains mediate semaphorin D/III-induced growth cone collapse. Neuron 21:1093-1100.

Naveilhan P, ElShamy W M, Ernfors P (1997) Differential regulation of mRNAs for GDNF and its receptors Ret and GDNFR alpha after sciatic nerve lesion in the mouse. Eur J Neurosci 9:1450-1460.

Neumann S, Woolf C J (1999) Regeneration of dorsal column fibers into and beyond the lesion site following adult spinal cord injury. Neuron 23:83-91.

Nielsch U, Keen P (1989) Reciprocal regulation of tachykinin- and vasoactive intestinal peptide-gene expression in rat sensory neurones following cut and crush injury. Brain Res 481:25-30.

Robinson N A, Lapic S, Welter J F, Eckert R L (1997) S100A11, S100A10, annexin I, desmosomal proteins, small proline-rich proteins, plasminogen activator inhibitor-2, and involucrin are components of the cornified envelope of cultured human epidermal keratinocytes. J Biol Chem 272:12035-12046.

Rosen CF, Poon R, Drucker D J (1995) UVB radiation-activated genes induced by transcriptional and posttranscriptional mechanisms in rat keratinocytes. Am J Physiol 268:C846-C855.

Sakaguchi M, Miyazaki M, Inoue Y, Tsuji T, Kouchi H, Tanaka T, Yamada H, Namba M (2000) Relationship between contact inhibition and intranuclear S100C of normal human fibroblasts. J Cell Biol 149:1193-1206.

Sasahara M, Fries J W, Raines E W, Gown A M, Westrum L E, Frosch M P, Bonthron D T, Ross R, Collins T (1991) PDGF B-chain in neurons of the central nervous system, posterior pituitary, and in a transgenic model. Cell 64:217-227.

Schecterson L C, Bothwell M (1992) Novel roles for neurotrophins are suggested by BDNF and NT-3 mRNA expression in developing neurons. Neuron 9:449-463.

Schnell L, Schneider R, Kolbeck R, Barde Y A, Schwab M E (1994) Neurotrophin-3 enhances sprouting of corticospinal tract during development and after adult spinal cord lesion. Nature 367:170-173.

Scotto C, Deloulme J C, Rousseau D, Chambaz E, Baudier J (1998) Calcium and S100B regulation of p53-dependent cell growth arrest and apoptosis. Mol Cell Biol 18:4272-4281.

Skene J H (1989) Axonal growth-associated proteins. Annu Rev Neurosci 12:127-156.

Skene J H, Willard M (1981) Axonally transported proteins associated with axon growth in rabbit central and peripheral nervous systems. J Cell Biol 89:96-103.

Stoll G, Griffin J W, Li C Y, Trapp B D (1989) Wallerian degeneration in the peripheral nervous system: participation of both Schwann cells and macrophages in myelin degradation. J Neurocytol 18:671-683. Su Q N, Namikawa K, Toki H, Kiyama H (1997) Differential display reveals transcriptional up-regulation of the motor molecules for both anterograde and retrograde axonal transport during nerve regeneration. Eur J Neurosci 9:1542-1547.

Takahashi T, Nakamura F, Jin Z, Kalb R G, Strittmatter S M (1998) Semaphorins A and E act as antagonists of neuropilin-1 and agonists of neuropilin-2 receptors. Nat Neurosci 1:487-493.

Takahashi T, Fournier A, Nakamura F, Wang L H, Murakami Y, Kalb R G, Fujisawa H, Strittmatter S M (1999) Plexin-neuropilin-1 complexes form functional semaphorin-3A receptors. Cell 99:59-69.

Tanabe K, Nakagomi S, Kiryu-Seo S, Namikawa K, Imai Y, Ochi T, Tohyama M, Kiyama H (1999) Expressed-sequence-tag approach to identify differentially expressed genes following peripheral nerve axotomy. Brain Res Mol Brain Res 64:34-40.

Tanabe K, Tachibana T, Yamashita T, Che Y H, Yoneda Y, Ochi T, Tohyama M, Yoshikawa H, Kiyama H (2000) The small GTP-binding protein TC10 promotes nerve elongation in neuronal cells, and its expression is induced during nerve regeneration in rats. J Neurosci 20:4138-4144.

Troy C M, Muma N A, Greene L A, Price D L, Shelanski M L (1990) Regulation of peripherin and neurofilament expression in regenerating rat motor neurons. Brain Res 529:232-238.

Villar M J, Cortes R, Theodorsson E, Wiesenfeld-Hallin Z, Schalling M, Fahrenkrug J, Emson P C, Hokfelt T (1989) Neuropeptide expression in rat dorsal root ganglion cells and spinal cord after peripheral nerve injury with special reference to galanin. Neuroscience 33:587-604.

Wakisaka S, Kajander K C, Bennett G J (1991) Increased neuropeptide Y (NPY)-like immunoreactivity in rat sensory neurons following peripheral axotomy. Neurosci Lett 124:200-203.

Wilkinson D G, Nieto M A (1993) Detection of messenger RNA by in situ hybridization to tissue sections and whole mounts. Methods Enzymol 225:361-373.

Wong J, Oblinger M M (1990) Differential regulation of peripherin and neurofilament gene expression in regenerating rat DRG neurons. J Neurosci Res 27:332-341.

Xiong Y, Hannon G J, Zhang H, Casso D, Kobayashi R, Beach D (1993) p21 is a universal inhibitor of cyclin kinases. Nature 366:701-704.

Yeh H J, Ruit K G, Wang Y X, Parks W C, Snider W D, Deuel T F (1991) PDGF A-chain gene is expressed by mammalian neurons during development and in maturity. Cell 64:209-216.

Zeng Y X, Somasundaram K, El-Deiry WS (1997) AP2 inhibits cancer cell growth and activates p21WAF1/CIP1 expression. Nat Genet 15:78-82.

Zhang Q, Shi T J, Ji R R, Zhang Y Z, Sundler F, Hannibal J, Fahrenkrug J, Hokfelt T, Zhang Y (1995) Expression of pituitary adenylate cyclase-activating polypeptide in dorsal root ganglia following axotomy: time course and coexistence. Brain Res 705:149-158.

Zigmond R E, Hyatt-Sachs H, Mohney R P, Schreiber R C, Shadiack A M, Sun Y, Vaccariello S A (1996) Changes in neuropeptide phenotype after axotomy of adult peripheral neurons and the role of leukemia inhibitory factor. Perspect Dev Neurobiol 4:75-90.

What is claimed is:

1. A method of inducing or increasing axonal growth from a dorsal root ganglia (DRG), the method comprising administering to a DRG a polypeptide encoded by a nucleic acid comprising SEQ ID NO: 1.

2. A method of inducing or increasing axonal growth from a dorsal root ganglia (DRG), the method comprising administering to a DRG a polypeptide comprising the amino acid sequence of SEQ ID NO: 2 or SEQ ID NO: 3.

3. The method of claim 1 or claim 2, wherein the DRG is in a mammal.

4. The method of claim 3, wherein the mammal is a human.

5. The method of claim 1 or claim 2, wherein the polypeptide is administered to the DRG following axotomy.

6. The method of claim 5, wherein the axotomy is sciatic nerve injury.

7. The method of claim 1 or claim 2, wherein the axonal growth is axonal regeneration.

* * * * *

SEQUENCE LISTING

<160> NUMBER OF SEQ ID NOS: 3

<210> SEQ ID NO 1
<211> LENGTH: 436
<212> TYPE: DNA
<213> ORGANISM: Mus musculus

<400> SEQUENCE: 1

```
atgagttccc accagcagaa gcagccctgc actgtacctc ctcagctgca ccagcagcag      60
gtgaagcagc cttgccagcc accacccag gaaccttgtg cccccaaaac caaggatccc     120
tgccaccctg ttcctgagcc ctgcaacccc aaggggccag agccctgcca ccccaaggca     180
cccgagccct gccaccccaa ggcacctgag ccctgcaacc caaggtgcc agagccctgc      240
cagcctaagg tgccagagcc ctgccagcct aaggtgccag agccctgcaa ccccaaggtg     300
ccagagccct gccaacctaa ggcaccagag ccttgccacc caaggcgcc tgagccctgc      360
caccctgttg ttcccgagcc ctgcccctca actgtcactc catcaccata ccagcagaag     420
acaaagcaga agtaat                                                    436
```

<210> SEQ ID NO 2
<211> LENGTH: 144
<212> TYPE: PRT
<213> ORGANISM: Mus musculus

<400> SEQUENCE: 2

```
Met Ser Ser His Gln Gln Lys Gln Pro Cys Thr Val Pro Pro Gln Leu
1               5                   10                  15

His Gln Gln Val Lys Gln Pro Cys Gln Pro Pro Gln Glu Pro
            20                  25                  30

Cys Ala Pro Lys Thr Lys Asp Pro Cys His Pro Val Pro Glu Pro Cys
            35                  40                  45

Asn Pro Lys Gly Pro Glu Pro Cys His Pro Lys Ala Pro Glu Pro Cys
        50                  55                  60

His Pro Lys Ala Pro Glu Pro Cys Asn Pro Lys Val Pro Glu Pro Cys
65                  70                  75                  80

Gln Pro Lys Val Pro Glu Pro Cys Gln Pro Lys Val Pro Glu Pro Cys
                85                  90                  95

Asn Pro Lys Val Pro Glu Pro Cys Gln Pro Lys Ala Pro Glu Pro Cys
            100                 105                 110

His Pro Lys Ala Pro Glu Pro Cys His Pro Val Val Pro Glu Pro Cys
            115                 120                 125

Pro Ser Thr Val Thr Pro Ser Pro Tyr Gln Gln Lys Thr Lys Gln Lys
    130                 135                 140
```

<210> SEQ ID NO 3
<211> LENGTH: 24
<212> TYPE: PRT
<213> ORGANISM: Mus musculus

<400> SEQUENCE: 3

```
His Pro Lys Ala Pro Glu Pro Cys Asn Pro Lys Val Pro Glu Pro Cys
1               5                   10                  15

Gln Pro Lys Val Pro Glu Pro Cys
            20
```